US011759188B2

(12) United States Patent
Matta et al.

(10) Patent No.: US 11,759,188 B2
(45) Date of Patent: Sep. 19, 2023

(54) DEVICES, SYSTEMS, AND METHODS FOR SPECIMEN REMOVAL

(71) Applicant: Covidien LP, Mansfield, MA (US)

(72) Inventors: George Matta, Plainville, MA (US); Matthew A. Dinino, Newington, CT (US); Saumya Banerjee, Hamden, CT (US); Gregory R. Morck, Haddam, CT (US); Jacob C. Baril, Norwalk, CT (US); Justin Thomas, New Haven, CT (US); Roy J. Pilletere, Middletown, CT (US); Kevin Desjardin, Prospect, CT (US)

(73) Assignee: Covidien LP, Mansfield, MA (US)

( * ) Notice: Subject to any disclaimer, the term of this patent is extended or adjusted under 35 U.S.C. 154(b) by 116 days.

(21) Appl. No.: 17/148,233

(22) Filed: Jan. 13, 2021

(65) Prior Publication Data

US 2021/0236104 A1 Aug. 5, 2021

Related U.S. Application Data

(60) Provisional application No. 63/120,435, filed on Dec. 2, 2020, provisional application No. 62/968,395, filed on Jan. 31, 2020.

(51) Int. Cl.
 *A61B 17/00* (2006.01)
(52) U.S. Cl.
 CPC .............. *A61B 17/00234* (2013.01); *A61B 2017/00287* (2013.01); *A61B 2017/00438* (2013.01)

(58) Field of Classification Search
 CPC .... A61B 17/00234; A61B 2017/00287; A61B 2017/00438
 See application file for complete search history.

(56) References Cited

U.S. PATENT DOCUMENTS

| | | | |
|---|---|---|---|
| 5,330,483 | A | 7/1994 | Heaven et al. |
| 5,735,289 | A | 4/1998 | Pfeffer et al. |
| 6,059,793 | A | 5/2000 | Pagedas |
| 6,156,055 | A | 12/2000 | Ravenscroft |
| 6,162,209 | A | 12/2000 | Gobron et al. |
| 6,171,317 | B1 | 1/2001 | Jackson et al. |
| 6,206,889 | B1 | 3/2001 | Bennardo |
| 6,224,612 | B1 | 5/2001 | Bates et al. |
| 6,228,095 | B1 | 5/2001 | Dennis |
| 6,248,113 | B1 | 6/2001 | Fina |
| 6,258,102 | B1 | 7/2001 | Pagedas |
| 6,264,663 | B1 | 7/2001 | Cano |
| 6,270,505 | B1 | 8/2001 | Yoshida et al. |

(Continued)

FOREIGN PATENT DOCUMENTS

WO 2011090867 A2 7/2011

OTHER PUBLICATIONS

Extended European Search Report issued in corresponding European Application No. 21154210.5 dated May 26, 2021, 10 pages.

*Primary Examiner* — Shaun L David
*Assistant Examiner* — Rachael L Geiger
(74) *Attorney, Agent, or Firm* — Carter, DeLuca & Farrell LLP

(57) ABSTRACT

Specimen retrieval bags, specimen retrieval devices, specimen retrieval systems, and specimen retrieval methods that are configured to facilitate the isolated removal of a tissue specimen from an internal body cavity such as, for example, during a minimally invasive surgical procedure.

18 Claims, 31 Drawing Sheets

(56) References Cited

U.S. PATENT DOCUMENTS

| | | |
|---|---|---|
| 6,280,451 B1 | 8/2001 | Bates et al. |
| 6,344,026 B1 | 2/2002 | Burbank et al. |
| 6,346,117 B1 | 2/2002 | Greenhalgh |
| 6,350,266 B1 | 2/2002 | White et al. |
| 6,350,267 B1 | 2/2002 | Stefanchik |
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,654,283 B2 | 2/2010 | Seto et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinski et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,542 B2 | 10/2016 | Hurley et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,624,638 B2 | 4/2017 | Lebreton et al. |
| 9,629,618 B2 | 4/2017 | Davis et al. |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 9,901,329 B1* | 2/2018 | Polo ............... A61B 17/32002 |
| 2011/0184431 A1* | 7/2011 | Parihar ............... A61B 17/00 |
| | | 606/114 |
| 2011/0184434 A1* | 7/2011 | Parihar ............ A61B 17/00234 |
| | | 606/114 |
| 2011/0184436 A1* | 7/2011 | Shelton, IV ...... A61B 17/00234 |
| | | 606/114 |
| 2011/0190779 A1* | 8/2011 | Gell ................. A61B 17/00234 |
| | | 606/114 |
| 2011/0299799 A1* | 12/2011 | Towe ............... A61B 17/00234 |
| | | 383/117 |
| 2020/0253639 A1* | 8/2020 | Kim ........................ A61B 17/29 |
| 2021/0322049 A1* | 10/2021 | Bleck .................. A61B 17/3205 |

\* cited by examiner

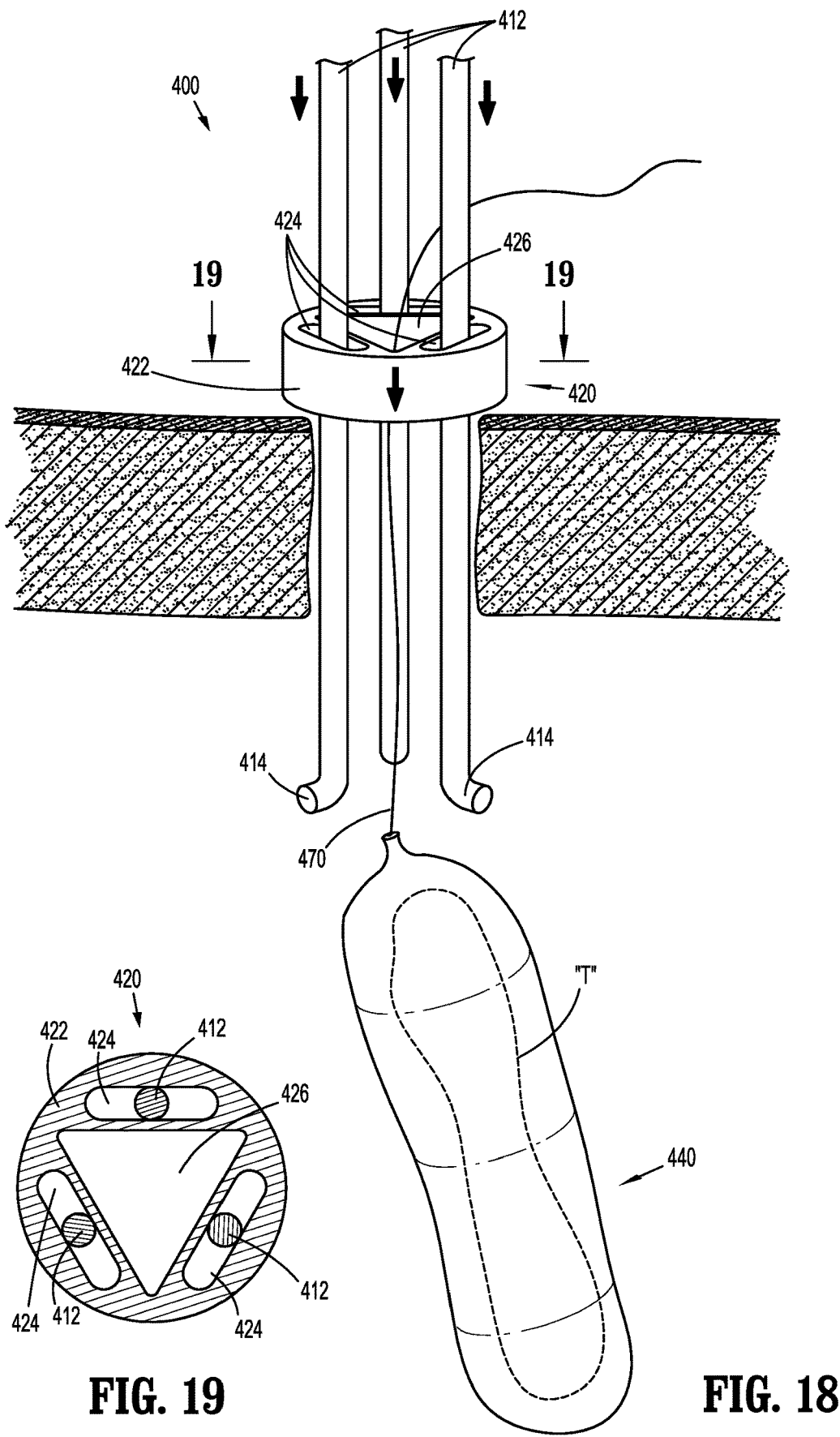
FIG. 19  FIG. 18

DEVICES, SYSTEMS, AND METHODS FOR SPECIMEN REMOVAL

CROSS-REFERENCE TO RELATED APPLICATIONS

This application claims the benefit of, and priority to, U.S. Provisional Patent Application No. 62/968,395, filed on Jan. 31, 2020, and U.S. Provisional Patent Application No. 63/120,435, filed on Dec. 2, 2020, the entire contents of each of which are hereby incorporated herein by reference.

FIELD

This disclosure is generally related to specimen retrieval and, more particularly, to devices, systems, and methods facilitating removal of a specimen from an internal body cavity

BACKGROUND

When removing certain specimen from an internal body cavity, e.g., diseased tissue, it may be desirable to inhibit contact between the specimen and surrounding tissue. In order to help protect surrounding tissue, specimen bags have been developed and utilized for deployment into an internal body cavity, loading of the specimen therein, and isolated removal of the specimen, thereby inhibiting contact between the specimen and surrounding tissue.

SUMMARY

This disclosure generally relates to specimen retrieval bags, specimen retrieval devices, specimen retrieval systems, and specimen retrieval methods configured to facilitate the isolated removal of a specimen from an internal body cavity such as, for example, during a minimally invasive surgical procedure.

A specimen retrieval device in accordance with aspects includes a tubular body having a proximal portion and a distal portion and defining a longitudinal lumen therethrough, an inner shaft slidably disposed within the longitudinal lumen of the tubular body, and a specimen bag. The inner shaft has a proximal portion, a distal portion, and a support member extending from the distal portion thereof. The specimen bag is supported on the support member of the inner shaft and includes a bag body having an open end connected to the support member of the inner shaft. The bag body defines a longitudinal axis. The specimen bag further includes a plurality of ribs connected to the bag body such that a respective longitudinal axis thereof is substantially parallel with the longitudinal axis of the bag body. The inner shaft is movable in relation to the tubular body from a first position wherein the support member and the specimen bag are disposed within the longitudinal lumen of the tubular body to a second position wherein at least a portion of the support member and the specimen bag are deployed externally of the tubular body.

In an aspect, the specimen bag includes a pull string including a distal portion threaded through the plurality of ribs and a proximal portion extending proximally from the distal through the tubular body.

In another aspect, the distal portion of the pull string winds around a circumference of the bag body of the specimen bag, from a location near the open end of the bag body to a location near a closed end of the bag body.

In another aspect, the distal portion of the pull string winds around the bag body in a helical manner through the plurality of ribs.

In still another aspect, a distal end of the distal portion of the pull string includes a stop member preventing the distal end portion of the pull string from being pulled out of a rib.

In yet another aspect, each rib includes at least one eyelet through which the distal portion of the pull string passes.

In still yet another aspect, each rib is linear.

In another aspect, the pull string is a first pull string and the specimen bag includes a second pull string including a distal portion threaded about the open end of the bag body and a proximal portion extending from the proximal portion of the tubular body.

In another aspect, the support member includes a pair of resilient fingers which support the specimen bag thereon and open the open end of the bag body in the second position.

Another specimen retrieval device in accordance with aspects includes a tubular body having a proximal portion and a distal portion and defining a longitudinal lumen therethrough, an inner shaft slidably disposed within the longitudinal lumen of the tubular body, and a specimen bag. The inner shaft has a proximal portion, a distal portion, and a support member connected to a distal end of the distal portion thereof. The specimen bag is supported on the support member of the inner shaft and includes a bag body having an open end connected to the support member of the inner shaft. The bag body defines a longitudinal axis. The specimen bag further includes a plurality of ribs connected to the bag body such that a respective longitudinal axis of each rib is substantially parallel with the longitudinal axis of the bag body, and a pull string. The pull string includes a distal portion slidably connected to the plurality of ribs and a proximal portion extending from the proximal portion of the tubular body. The inner shaft is movable in relation to the tubular body from a first position wherein the support member and the specimen bag are disposed within the longitudinal lumen of the tubular body to a second position wherein at least a portion of the support member and the specimen bag are deployed externally of the tubular body. In the second position, the bag body is free to expand to a maximum radial dimension thereof. The pull string is actuatable to radially constrict the radial dimension of the bag body by drawing the plurality of ribs radially inwardly towards the longitudinal axis of the bag body.

In an aspect, the distal portion of the pull string winds around a circumference of the bag body of the specimen bag, from a location near the open end of the bag body to a location near a closed end of the bag body.

In another aspect, the distal portion of the pull string winds around the bag body in a helical manner through the plurality of ribs.

In still another aspect, a distal end of the distal portion of the pull string includes a stop member preventing the distal end portion of the pull string from being pulled out of a rib.

In yet another aspect, each rib includes at least one eyelet through which the distal portion of the pull string passes.

Each rib, in aspects, may be linear.

In still yet another aspect, the pull string is a first pull string and the specimen bag includes a second pull string including a distal portion threaded about the open end of the bag body and a proximal portion extending from the proximal portion of the tubular body.

In yet another aspect, the support member includes a pair of resilient fingers which support the bag body of the specimen bag and open the open end of the bag body in the second position.

A specimen bag provided in accordance with aspects includes a bag body having an open end and defining a longitudinal axis, a plurality of ribs connected to the bag body such that a respective longitudinal axis of each rib is substantially parallel with the longitudinal axis of the bag body, and a pull string. The pull string includes a distal portion slidably connected to the plurality of ribs, a proximal portion extending proximally from the distal portion to enable selective actuation thereof, and a stop member connected to a distal end of the pull string. The stop member prevents the distal end portion of the pull string from being pulled out of a rib. In an initial condition, the bag body is free to expand to a maximum radial dimension thereof. The pull string is actuatable to radially constrict the radial dimension of the bag body from the initial condition by drawing the distal portion of the pull string through the plurality of ribs to draw the plurality of ribs radially inwardly towards the longitudinal axis of the bag body.

In an aspect, the distal portion of the pull string winds around the bag body in a helical manner through the plurality of ribs. Additionally or alternatively, each rib is linear.

Another specimen bag in accordance with aspects includes a bag body and a suction tube wound about the bag body in a helical pattern. When suction is applied through the suction tube, a diameter of the helix defined by the suction tube is reduced, thereby constricting the specimen bag and compressing a specimen disposed therein.

In accordance with still other aspects of the disclosure, a specimen retrieval system is provided including an outer cannula and an inner cannula. The outer cannula includes a first tubular body having a first inner surface defining a first longitudinal passageway. The first tubular body is configured for positioning within an opening in tissue. The inner cannula includes a second tubular body having a second inner surface defining a second longitudinal passageway. The second tubular body is positionable within the first longitudinal passageway and rotatable relative thereto. The second inner surface includes helical threading configured to facilitate feeding tissue proximally through the second longitudinal passageway upon rotation of the inner cannula relative to the outer cannula.

In an aspect of the disclosure, the helical threading protrudes from the second inner surface. Alternatively, the helical threading may be recessed into the second inner surface.

In another aspect of the disclosure, the outer cannula further includes a proximal hub disposed at a proximal end portion of the first tubular body. Additionally or alternatively, the inner cannula further includes a proximal hub disposed at a proximal end portion of the second tubular body.

In yet another aspect of the disclosure, the first inner surface and an outer surface of the second tubular body are smooth to facilitate relative rotation between the first and second tubular bodies.

In still another aspect of the disclosure, the system further includes a grasper configured for insertion through the second longitudinal passageway and to draw tissue proximally through the second longitudinal passageway. In aspects, the inner cannula is configured to rotate relative to the grasper.

In still yet another aspect of the disclosure, the system further includes a specimen bag. In aspects, the specimen bag is configured to receive tissue therein and to be withdrawn through the second longitudinal passageway along with tissue received therein. In other aspects, the outer and inner cannulas are configured for positioning within the specimen bag to enable withdrawal of tissue within the specimen bag proximally through the second longitudinal passageway. In still other aspects, the outer cannula is configured to revive the specimen bag through the first longitudinal passageway and the inner cannula is configured for positioning within the specimen bag to enable withdrawal of tissue within the specimen bag proximally through the second longitudinal passageway.

Yet another specimen retrieval system provided in accordance with aspects of the disclosure includes a specimen bag including a bag body and a biaxial structure, and an insert. The biaxial structure is transitionable between a first condition wherein the specimen bag defines a longitudinally compressed and radially expanded configuration, and a second condition, wherein the specimen bag defines a longitudinally expanded and radially compressed configuration. The insert is positionable within the specimen bag and configured to maintain at least a portion of the biaxial structure in the first condition.

In an aspect of the disclosure, the biaxial structure is biased towards the first condition. Alternatively, the biaxial structure may be biased towards the second condition.

In another aspect of the disclosure, the specimen bag further includes a reinforcement ring surrounding a mouth of the bag body, e.g., to maintain the open mouth in an open condition.

In yet another aspect of the disclosure, the bag body is configured to stretch to accommodate transitioning of the biaxial structure between the first and second conditions.

In still another aspect of the disclosure, the insert includes a plurality of fingers extending from a common end portion. Alternatively, the insert may include a plurality of fingers extending from a base ring. In either aspect, the insert may be compressible from an initial condition to a compressed condition.

In still yet another aspect of the present disclosure, the biaxial structure is disposed within the bag body. Alternatively, the biaxial structure may be disposed about the bag body.

Another specimen retrieval system provided in accordance with aspects of the disclosure includes a plurality of rods configured for insertion through an opening in tissue and arrangement to define a longitudinal passageway through the opening in tissue. The system further includes at least one collar configured for slidable positioning about the plurality of rods to maintain the longitudinal passageway. Each of the at least one collars defines a central opening in communication with the longitudinal passageway to enable withdrawal of tissue through the longitudinal passageway and each central opening.

In an aspect of the disclosure, the at least one collar is configured for sliding about the plurality of rods through the opening in tissue.

In another aspect of the disclosure, the at least one collar includes a plurality of collars configured for spaced-apart positioning along at least a portion of a length of the plurality of rods.

In yet another aspect of the disclosure, each of the at least one collars defines a plurality of discrete openings. Each discrete opening is configured to slidably receive one of the rods of the plurality of rods. The discrete openings may be slots to enable the rods to slide along the respective slots to permit repositioning of the rods relative to one another.

In still another aspect of the disclosure, each of the rods defines a stop at a distal end thereof to inhibit the at least one collar from sliding distally off of the rods.

In still yet another aspect of the disclosure, the central opening defines a non-circular cross-section, e.g., a triangular cross-section.

In another aspect of the disclosure, each collar defines a cylindrical disc-shape.

In aspects, the system may further include a specimen bag configured for positioning within an internal surgical site. The specimen bag is configured to be pulled through the longitudinal passageway and each central opening to enable withdrawal of the specimen bag from the internal surgical site.

In aspects, a pull-string is connected to the specimen bag towards an open end thereof and configured to facilitate pulling the specimen bag.

Still another specimen retrieval system, and an associated method, in accordance with aspects includes a tube, a specimen bag, a connector connecting the tube with the specimen bag (permanently or releasably), and a pump and suction source. With a specimen disposed within the specimen bag and the specimen bag closed, the pump and suction source is activated in a pump mode to pump fluid through the tube and into the specimen bag, thereby compressing a specimen therein to squeeze fluids out of the specimen. The pump and suction source is then activated in a suction mode to suction out the fluid from the specimen bag through the tube. The reduced-volume (as a result of the squeezed and removed fluid) specimen within the specimen bag can then be more readily removed via removal of the specimen bag.

Still another specimen bag in accordance with aspects includes a bag body and a tie arrangement disposed on, within, and/or integrated into the bag body. The tie arrangement includes at least one strand of material forming a netting having an initial, first condition having a first diameter. In response to a longitudinal pulling force applied to one of the strands of the tie arrangement, the netting transitions to a second condition, wherein the netting has a second, smaller diameter such that the specimen bag is constricted, thereby compressing a specimen disposed therein.

A method of specimen removal in accordance with aspects includes positioning a specimen within a specimen bag, tightening a pull string about a portion of the specimen bag having a portion of the specimen therein such that the pull string grasps the portion of the specimen bag and the portion of the specimen, and pulling the pull string to withdraw the specimen bag, with the specimen therein, from an internal body cavity.

Still yet another specimen retrieval system in accordance with aspects includes a cannula, a funnel, and a gear assembly. The gear assembly operably couples the funnel about the cannula to enable ratcheted distal sliding of the funnel about the cannula, e.g., to compress a specimen within a distal cone portion of the funnel. The specimen may be removed through the funnel and the cannula, wherein the distal cone portion of the funnel reduces withdrawal forces. The specimen may be removed itself (e.g., wherein the specimen retrieval system is inserted into a specimen bag containing the specimen) or may be removed through the funnel and cannula together with a specimen bag retaining the specimen therein.

Another specimen retrieval system in accordance with aspects includes a specimen bag configured for positioning within an internal surgical site and a body. The specimen bag includes an open end and a closed end and has first and second racks disposed on an outer surface thereof on opposing sides thereof. The body includes a ratchet assembly having first and second ratchet gears. The specimen bag is configured for passage through the body such that the first and second racks engage the first and second ratchet gears to enable ratcheted passage of the specimen back through the body.

The details of one or more aspects of the disclosure are set forth in the accompanying drawings and the description below. Other features, objects, and advantages of the disclosure will be apparent from the description and drawings, and from the claims.

BRIEF DESCRIPTION OF DRAWINGS

FIG. 18 is a perspective view illustrating another specimen retrieval device in use within an internal body cavity;

FIG. 19 is a transverse, cross-sectional view taken across section line 19-19 of FIG. 18;

DETAILED DESCRIPTION

This disclosure provides devices, systems, and methods facilitating removal of a specimen from an internal body cavity such as, for example, for use in minimally invasive surgical procedures including but not limited to laparoscopic procedures, arthroscopic procedures, endoscopic procedures, natural orifice transluminal endoscopic surgical (NOTES) procedures, etc.

Figure 1:
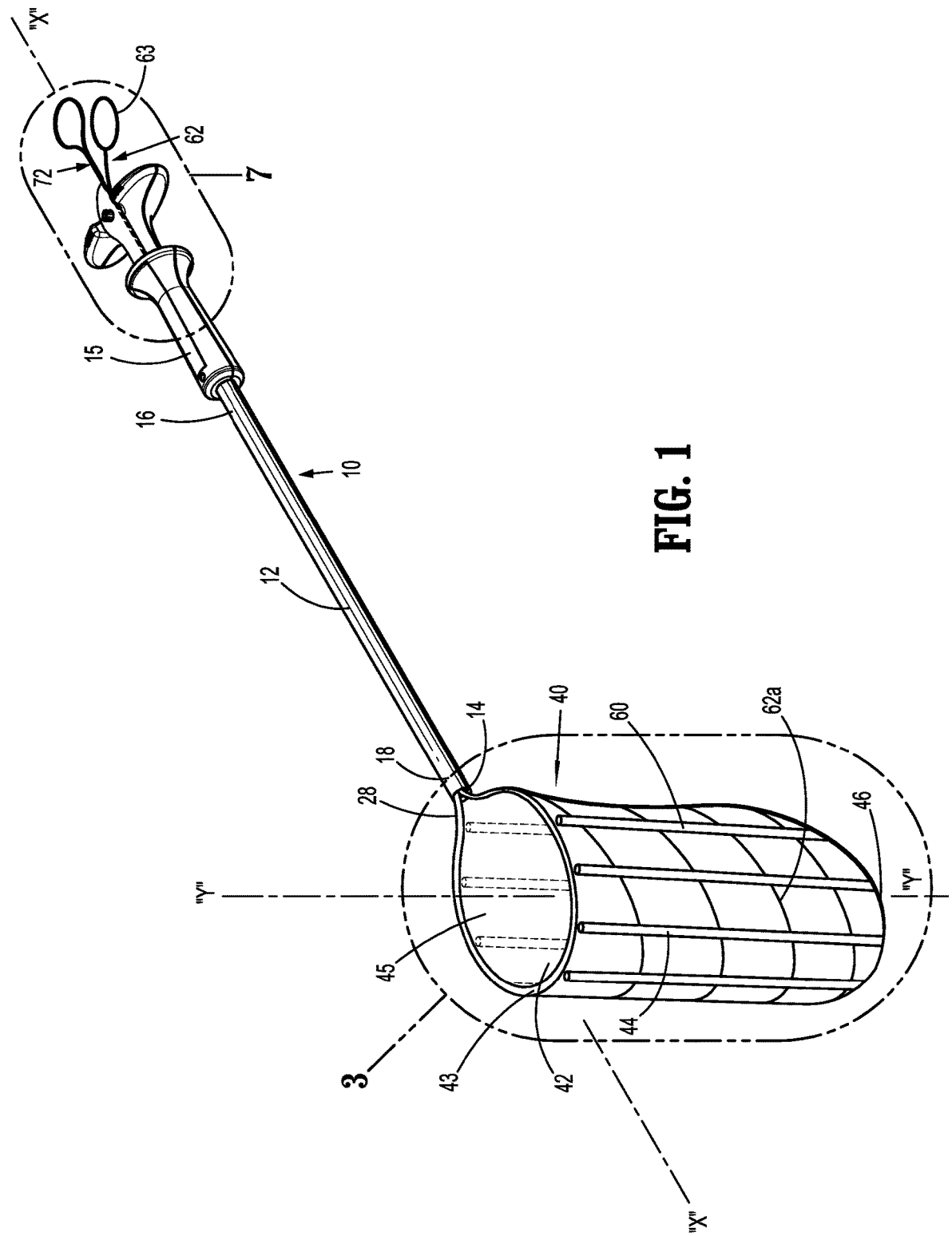
FIG. 1 is a perspective view of a specimen retrieval device disposed in a deployed condition.
Figure 2:
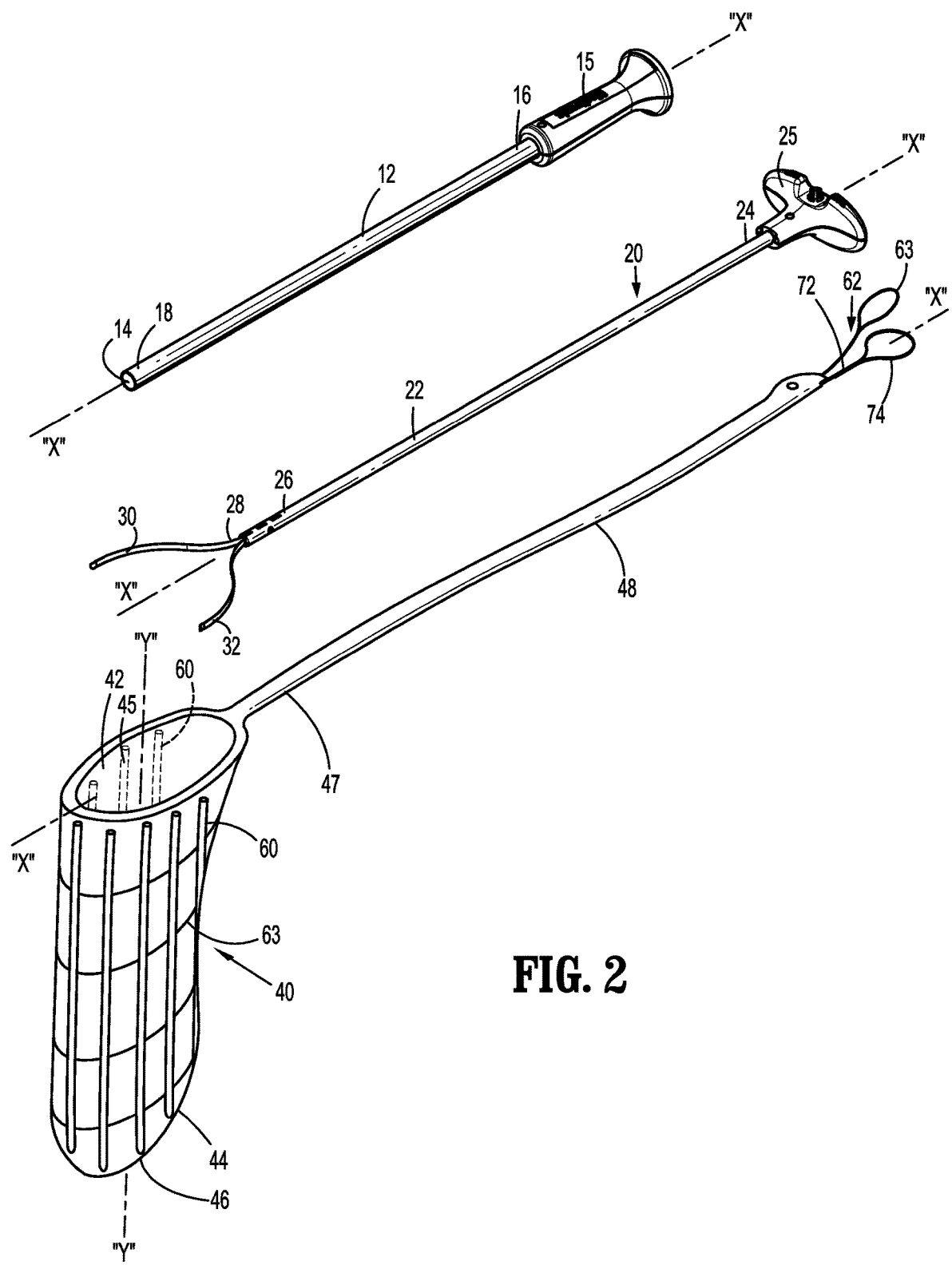
FIG. 2 is a perspective view, with parts separated, of the specimen retrieval device of FIG. 1.

Referring to FIGS. 1 and 2, a specimen retrieval device 10 includes a tubular body 12 having a proximal portion 16 and a distal portion 18, and defining a longitudinal lumen 14 that extends between proximal portion 16 and distal portion 18. Proximal portion 16 of tubular body 12 supports a hand grip 15. Specimen retrieval device 10 also includes an inner shaft assembly 20 having an inner shaft 22 slidably positioned within longitudinal lumen 14 of tubular body 12, an actuation handle 25 secured to a proximal portion 24 of inner shaft 22, and a specimen bag 40 supported on a distal portion 26 of inner shaft 22. Tubular body 12 and inner shaft 22 define a common longitudinal axis "X."

Hand grip 15 and actuation handle 25 are configured for concomitant and relative manipulation to facilitate manipulation of specimen retrieval device 10 and the sliding of inner shaft 22 within tubular body 12. More specifically, hand grip 15 and actuation handle 25 can be moved together to manipulate specimen retrieval device 10 to a desired position and, thereafter, hand grip 15 can be grasped with one hand and actuation handle 25 can be grasped with the other hand to affect relative movement therebetween to move inner shaft 22 within tubular body 12.

Distal portion 26 of inner shaft 22 is coupled to a support member 28 that is configured to support a mouth 42 of a specimen bag 40. Support member 28 includes a pair of resilient fingers 30, 32 that extend distally from distal portion 26 of inner shaft 22. Resilient fingers 30, 32 may be integrally formed with distal portion 26 of inner shaft 22 such as by molding. Alternatively, a retention pin (not shown) or other suitable attachment mechanism may be used to attach resilient fingers 30, 32 to distal portion 26 of inner shaft 22. Resilient fingers 30, 32 are movable from a further-spaced, un-flexed position (not shown) to a further-approximated, flexed position (FIG. 1) such as, for example, to enable placement and retention of resilient fingers 30, 32 and specimen bag 40 within tubular body 12. Resilient fingers 30, 32 return to the further-approximated, flexed position when deployed from tubular body 12 to thereby deploy specimen bag 40 and present mouth 42 of specimen bag 40, as described below.

Specimen bag 40 includes a bag body 44 having a generally tubular, elongated sock-like configuration that is defined by an openable and closable mouth 42 and a closed end 46 (FIG. 1). Mouth 42 defines an opening 45. In embodiments, specimen bag 40 includes a tail 48 (FIG. 2) having a neck region 47 defined along longitudinal axis "X" while bag body 44 of specimen bag 40 defines a longitudinal axis "Y" (FIG. 2) disposed at an angle relative to longitudinal axis "X."

With continued reference to FIGS. 1 and 2, bag body 44 defines a maximum radial dimension sufficient for receiving and containing a tissue specimen therein and may be made from any suitable biocompatible material (e.g., nylon, urethane, ripstop nylon, latex, etc.) capable of forming a flexible collapsible membrane. In embodiments, portions of specimen bag 40 are made of two different materials (e.g., two different nylons) secured together to form areas of specimen bag 40 having high strength.

Mouth 42 of specimen bag 40 is releasably connected to resilient fingers 30, 32 of inner shaft 22 such as, for example, via recite of resilient fingers 30, 32 within one or more cuff 43 defined about mouth 42 of specimen bag 40.

Specimen retrieval device 10 further includes a pull string 70 having a distal portion attached to and encircling mouth 42 of specimen bag 40. In embodiments, resilient fingers 30, 32 and pull string 70 may both be received in the one or more cuffs 43 of specimen bag 40, or may be received within separate cuffs 43 or other suitable retaining structures defined about mouth 42 of specimen bag 40.

Figure 7:
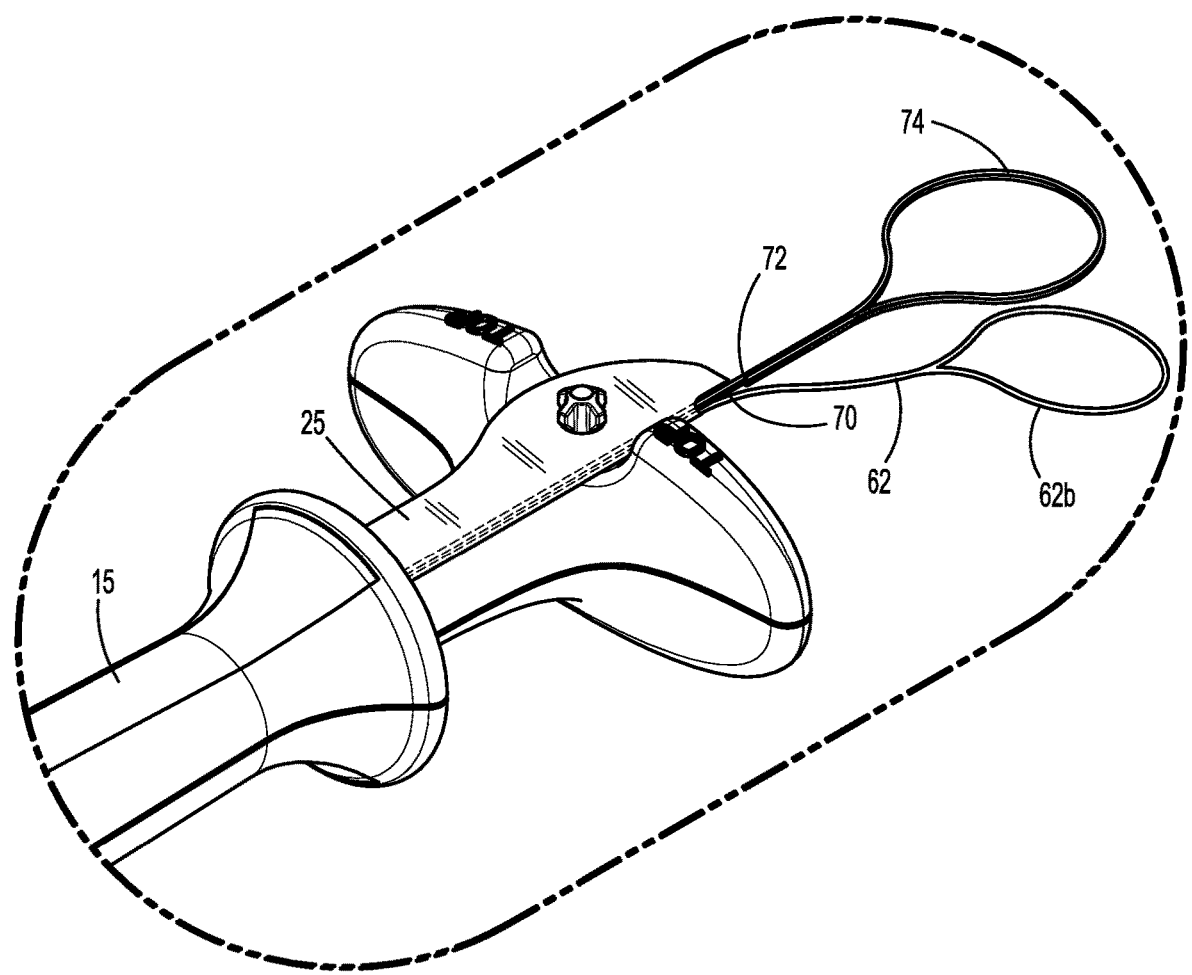
FIG. 7 is an enlarged, perspective view of the area of detail indicated as "7" in FIG. 1.

Referring also to FIG. 7, a proximal portion 72 of pull string 70 may be in the form of a loop 74 to assist in pulling pull string 70, thereby tightening the distal portion of pull string 70 and, in turn, closing mouth 42 of specimen bag 40.

FIGS. 2-6 illustrate specimen bag 40, which includes a plurality of ribs 60 connected to bag body 44. Ribs 60 are disposed radially about bag body 44. Ribs 60 are oriented such that longitudinal axes thereof are substantially parallel with longitudinal axis "Y" of bag body 44. In embodiments, the longitudinal axes of ribs 60 may be parallel to longitudinal axis "Y" of the bag body 44 (e.g., having a zero degree (0°) orientation angle therebetween), or may define orientation angles of up to about 45° therebetween.

Ribs 60 may be located externally of bag body 44, internally of bag body 44 or interposed between layers of material forming bag body 44, either entirely or partially, or any combination thereof. Further, while linear ribs 60 are shown and described, it is contemplated that ribs 60 may be angled or define a helical or curved configuration. The configuration, number, and a dimensions of ribs 60 are selected such that specimen bag 40 may be sufficiently collapsed to reside within lumen 14 of tubular body 12. In embodiments, ribs 60 are substantially rigid to resist bending and deformation.

With additional reference to FIG. 7, specimen bag 40 further includes a pull string 62 having a distal portion 63 threaded through plurality of ribs 60 in a helical pattern about bag body 44 of specimen bag 40 to encircle bag body 44 of specimen bag 40. More specifically, pull string 62 slidably passes through apertures 61 defined through each rib 60. A distal-most end of pull string 62 may be provided with a stop member 64, e.g., a knot, enlarged head, etc., which prevents withdrawal of the distal-most end of pull string 62 from within the last rib 60. While a single pull string 62 is shown and described, it is contemplated that any number of pull strings 62 may be provided, and may wrap around bag body 44 and through ribs 60 in one or more directions (e.g., a crisscrossing helical pattern) to facilitate constricting bag body 44 and ribs 60 radially inward along an entire length of bag body 44 of specimen bag 40 when the pull string(s) 62 is are pulled proximally.

Referring to FIGS. 1, 2, 8 and 9, in use, tubular body 12 of specimen retrieval device 10 is inserted into an internal surgical site with specimen bag 40 positioned within tubular body 12, e.g., furled about inner shaft 22 or disposed distally thereof. When it is desired to deploy specimen bag 40 within the internal surgical site, actuation handle 25 is pushed distally relative to hand grip 15 such that distal portion 26 of inner shaft 22 urges specimen bag 40 to exit distal portion 18 of tubular body 12.

Once specimen bag 40 has exited tubular body 12, resilient fingers 30, 32 return under bias to their further-spaced, non-flexed condition, thereby opening mouth 42 of specimen bag 40 to ensure specimen bag 40 is deployed. As mouth 42 of specimen bag 40 is opened, and due to bag body 44 of specimen bag 40 being free of tubular body 12, a specimen may be introduced into bag body 44 of specimen bag 40 through opening 45 of mouth 42.

Figure 8:
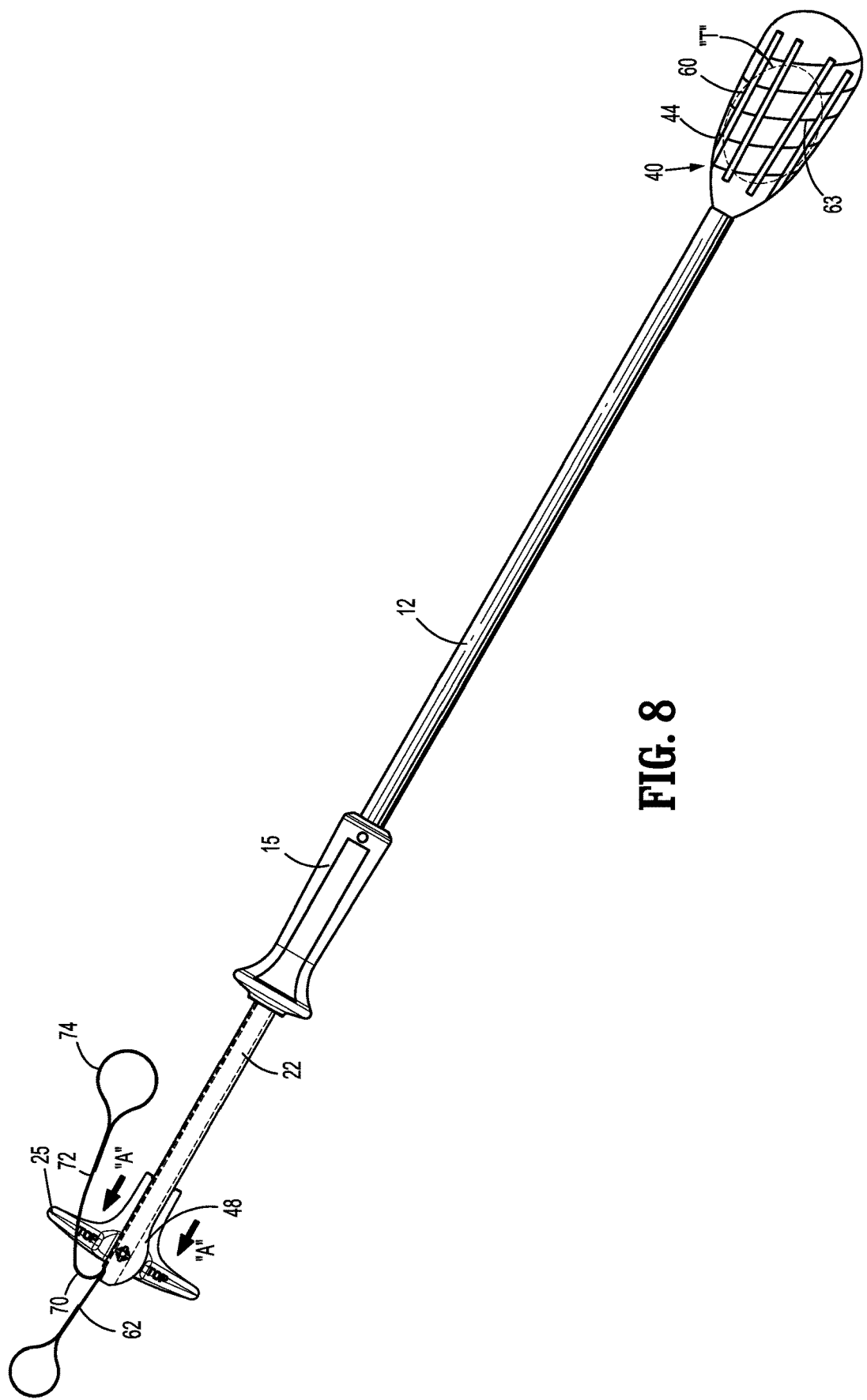
FIG. 8 is a perspective view of the specimen retrieval device of FIG. 1 disposed in a first partially-retracted condition.
Figure 9:
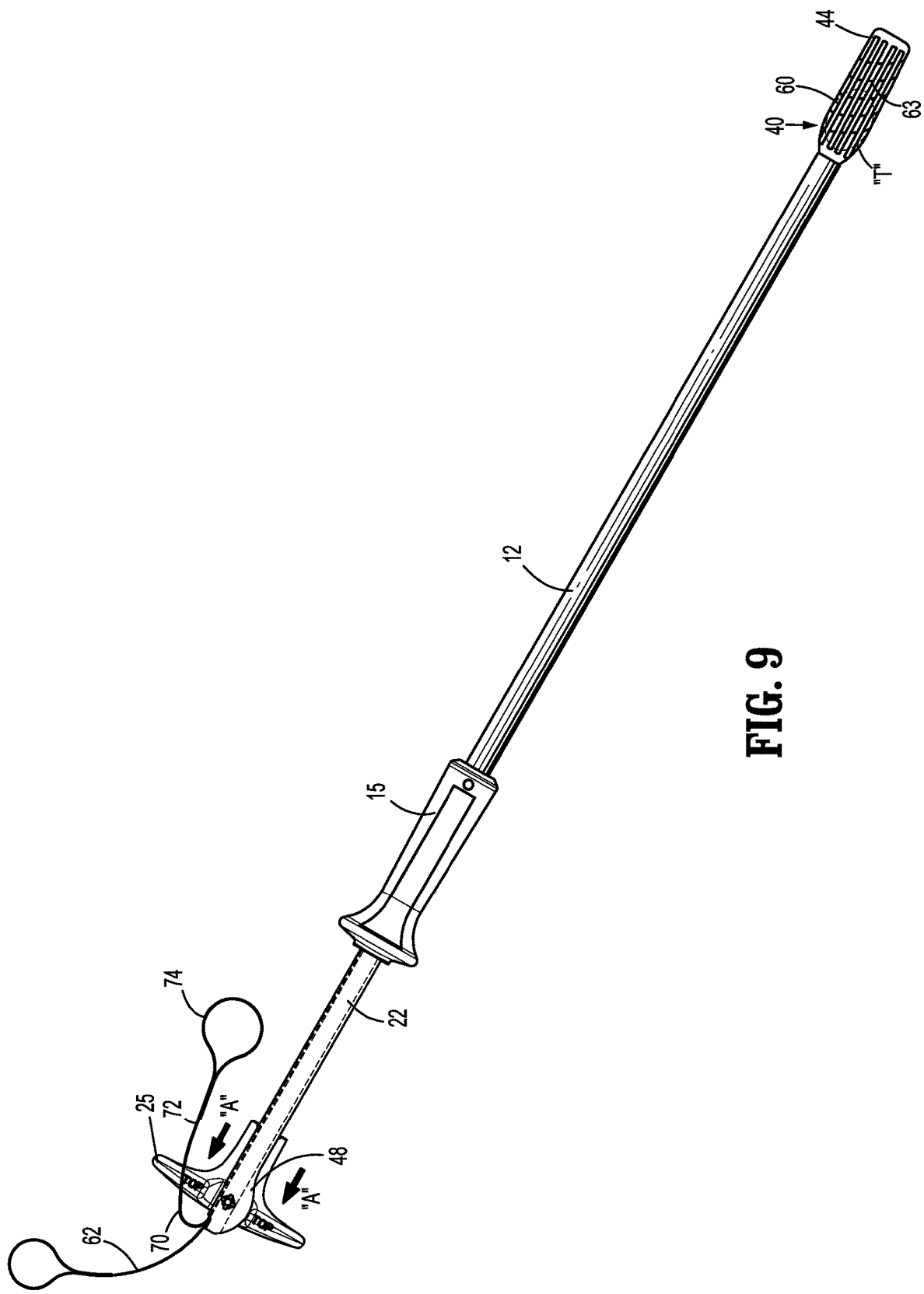
FIG. 9 is a perspective view of the specimen retrieval device of FIG. 1 disposed in a second partially-retracted condition.

As depicted in FIG. 8, after a specimen, e.g., tissue "T," has been placed in specimen bag 40, pull string 70 is pulled proximally (indicated by arrows "A" in FIG. 8), thus closing mouth 42 of specimen bag 40 and withdrawing a portion of specimen bag 40 into tubular body 12. After mouth 42 is closed, as depicted in FIG. 9, pull string 62 is pulled proximally (indicated by arrows "A" in FIG. 9), thus pulling distal portion 63 of pull string 62 through ribs 60 to radially inwardly contract and approximate ribs 50. As a result, bag body 44 of specimen bag 40 is compressed, thereby reducing a transverse cross-sectional dimension of specimen bag 40, including tissue "T" therein. The orientation of ribs 60 and positioning thereof about bag body 44, together with the arrangement of pull string 62 relative to ribs 60 provides uniform compression about tissue "T" when pull string 62 is pulled proximally.

With specimen bag 40 retaining tissue "T" therein and disposed in a closed and contracted condition, tail 48 of specimen bag 40 and/or inner shaft 22 may be withdrawn proximally to withdraw specimen bag 40 from the body cavity through lumen 14 of tubular body 12 or together therewith.

Figure 3:
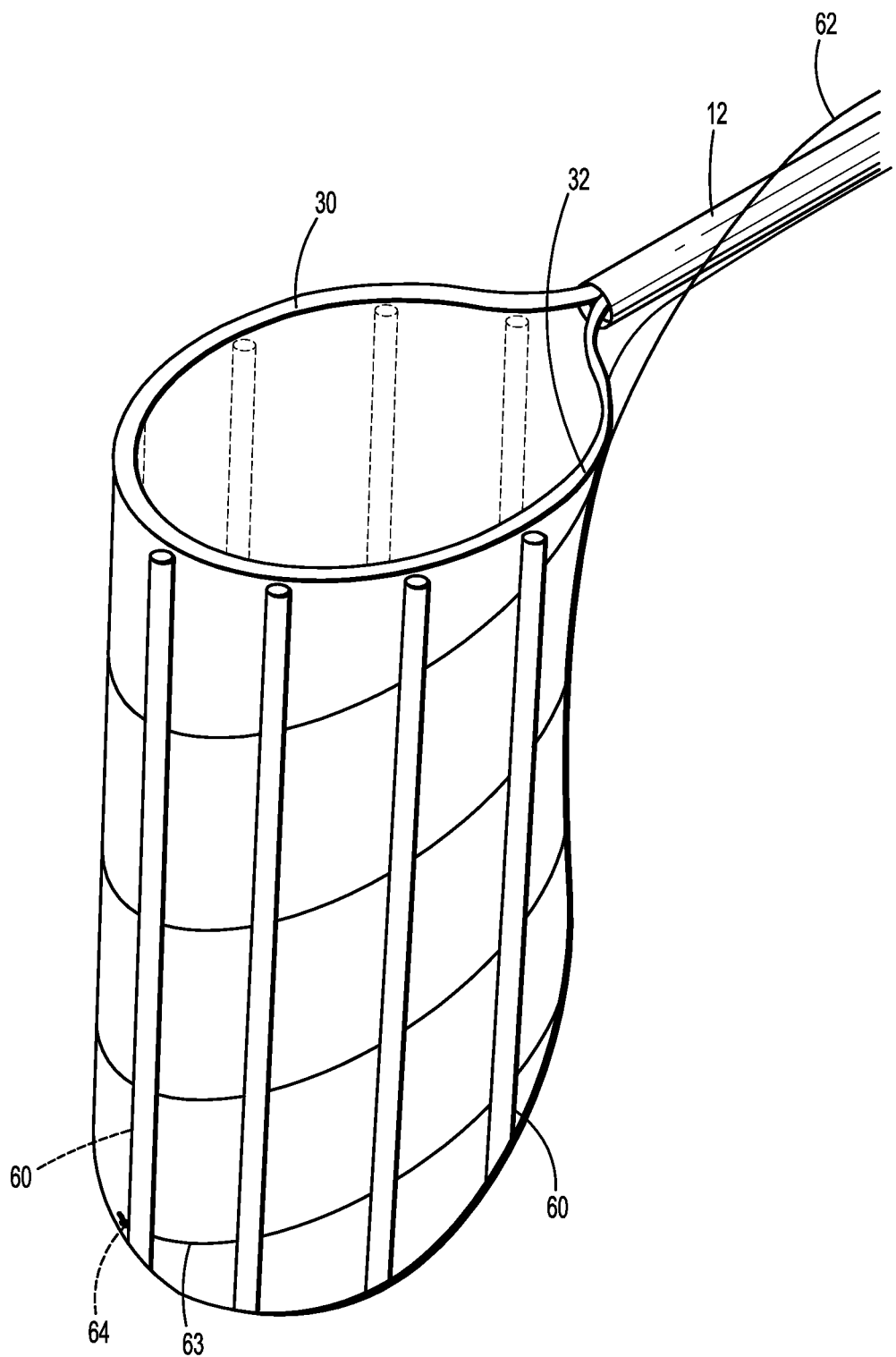
FIG. 3 is an enlarged, perspective view of the area of detail indicated as "3" in FIG. 1, illustrating a specimen bag of the specimen retrieval device of FIG. 1, disposed in an expanded condition.
Figure 4:
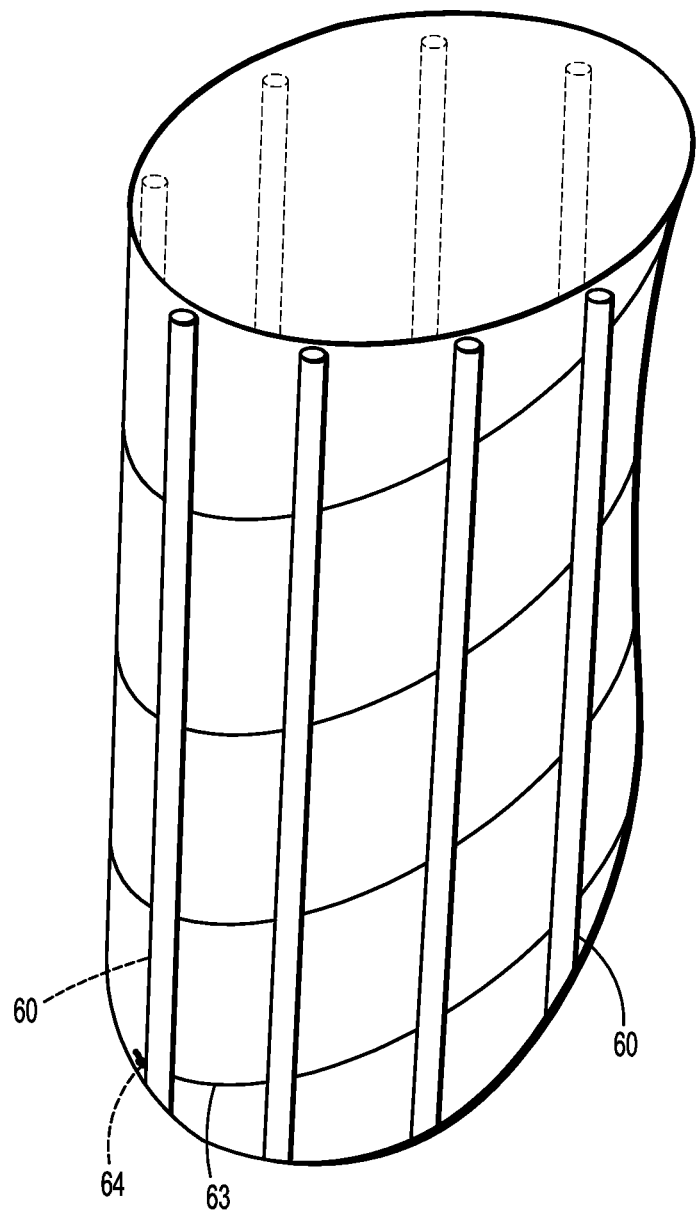
FIG. 4 is a perspective view of the specimen bag of FIG. 3 disposed in the expanded condition.
Figure 6:
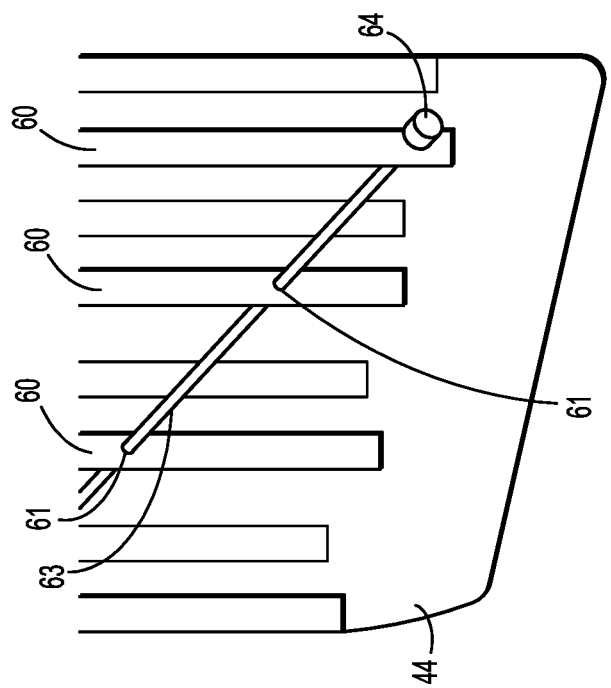
FIG. 6 is a greatly enlarged, side view of a portion of the specimen bag of FIG. 3.
Figure 5:
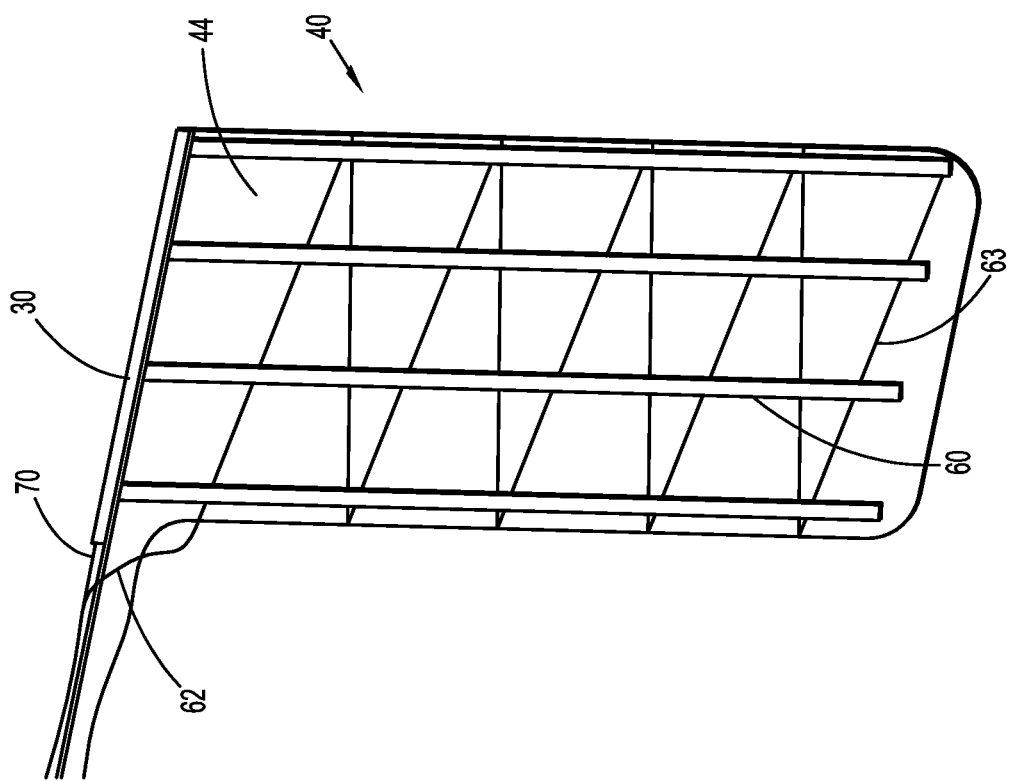
FIG. 5 is an enlarged, side view of the specimen bag of FIG. 3 disposed in a contracted condition.
Figure 10:
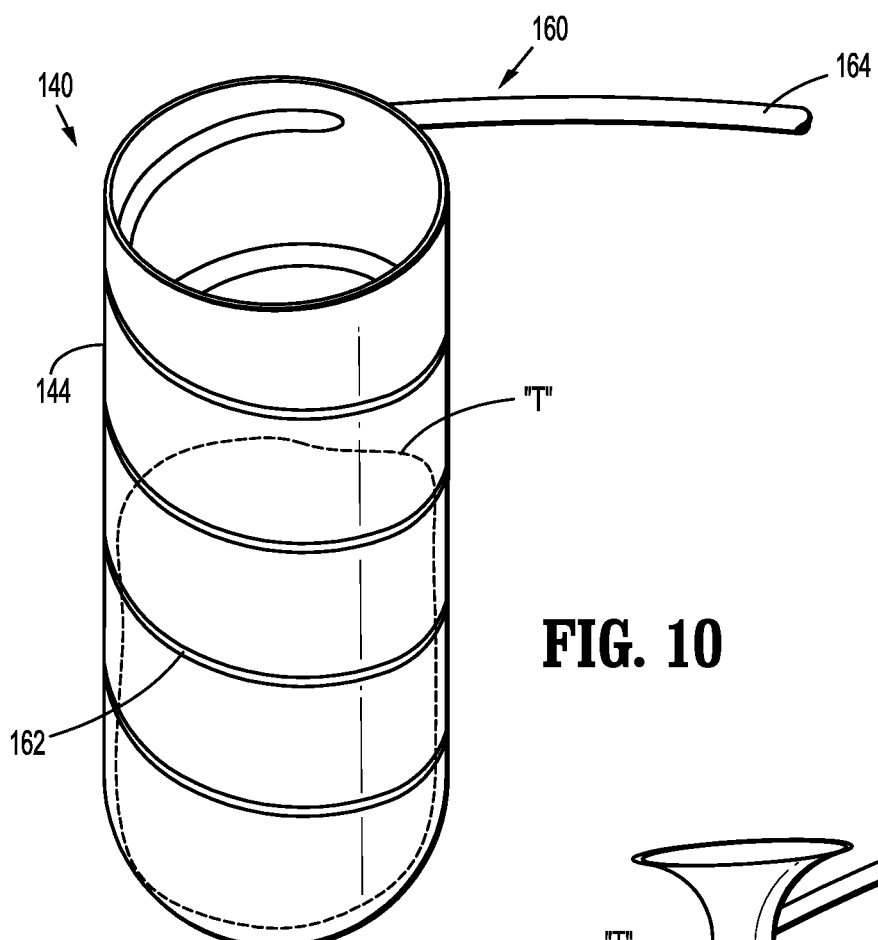
FIG. 10 is a perspective view of another specimen bag configured for use with the specimen retrieval device of FIG. 1, any other suitable specimen retrieval device, or as a standalone specimen bag, disposed in an expanded condition.
Figure 11:
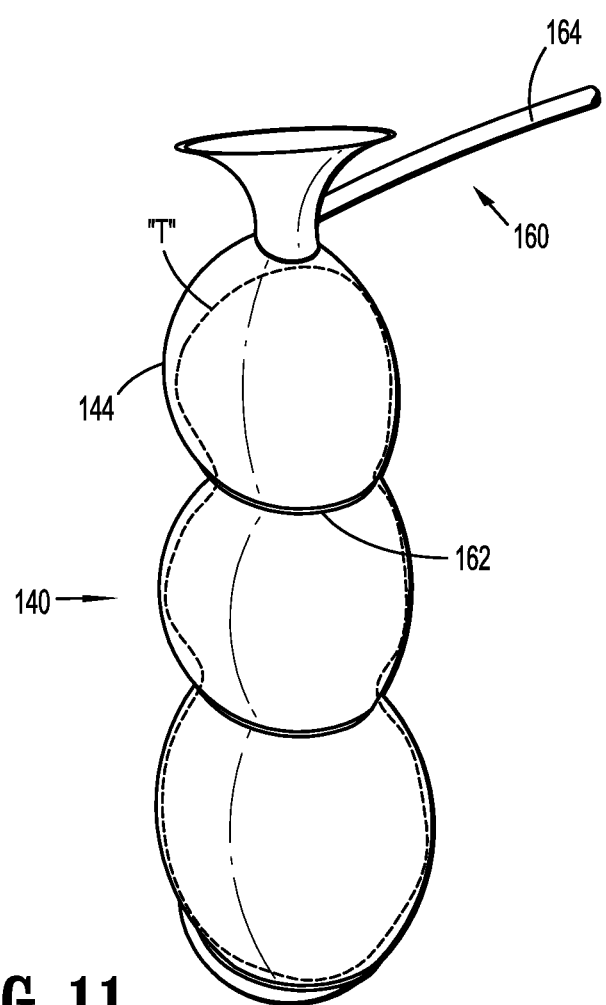
FIG. 11 is a perspective view of the specimen bag of FIG. 10, disposed in a contracted condition.

Turning to FIGS. 10 and 11, another specimen bag 140 configured for use with specimen retrieval device 10 (FIG. 1), any other suitable specimen retrieval device, or as a standalone specimen bag is shown. Specimen bag 140 may include any of the features of specimen bag 40 (FIGS. 1-6) except that, rather than including ribs 60 and a pull string 62 as specimen bag 40 (see FIGS. 2-4), specimen bag 140 includes a suction tube 160. However, it is also contemplated that specimen bag 140 include both suction tube 160 and ribs similar to ribs 60 (FIGS. 2-4).

Suction tube 160 may be disposed externally of bag body 144 of specimen bag 140, internally of bag body 144 or interposed between layers of material forming bag body 144, either entirely or partially, or any combination thereof. Suction tube 160 includes a helical body 162 that defines a helical configuration extending about bag body 144. Suction tube 160 further includes a proximal extension 164 that extends from helical body 162 and bag body 144, e.g., proximally through tubular body 12 (FIG. 1), to connect to a source of suction (not shown).

FIG. 10 illustrates specimen bag 140 in an expanded condition prior to activation of suction. As shown in FIG. 11, upon activation of suction through suction tube 160, helical body 162 is contracted radially inwardly to thereby compress bag body 144 and any tissue "T" within bag body 144 radially inwardly, reducing a transverse cross-sectional dimension of specimen bag 140 to facilitate removal from an internal surgical site.

The helical configuration of suction tube 160 provides radial inward compression about the entire circumference of bag body 144, thus providing more uniform compression about tissue "T." In embodiments, multiple suction tubes 160 are provided, e.g., two suction tubes 160 defining a double helix, to further facilitate uniform compression about tissue "T."

Figure 12:
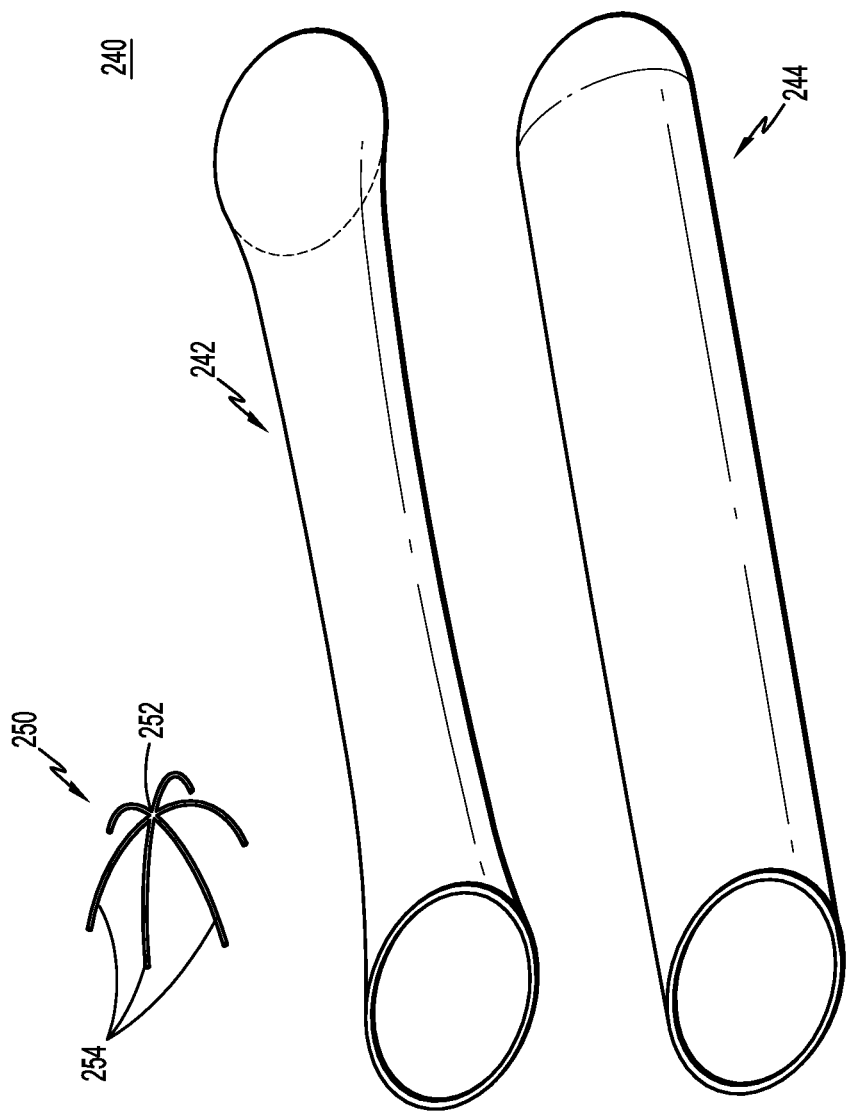
FIG. 12 is an exploded, perspective view of another specimen bag configured for use with the specimen retrieval device of FIG. 1, any other suitable specimen retrieval device, or as a standalone specimen bag, disposed in an expanded condition.
Figure 13A:
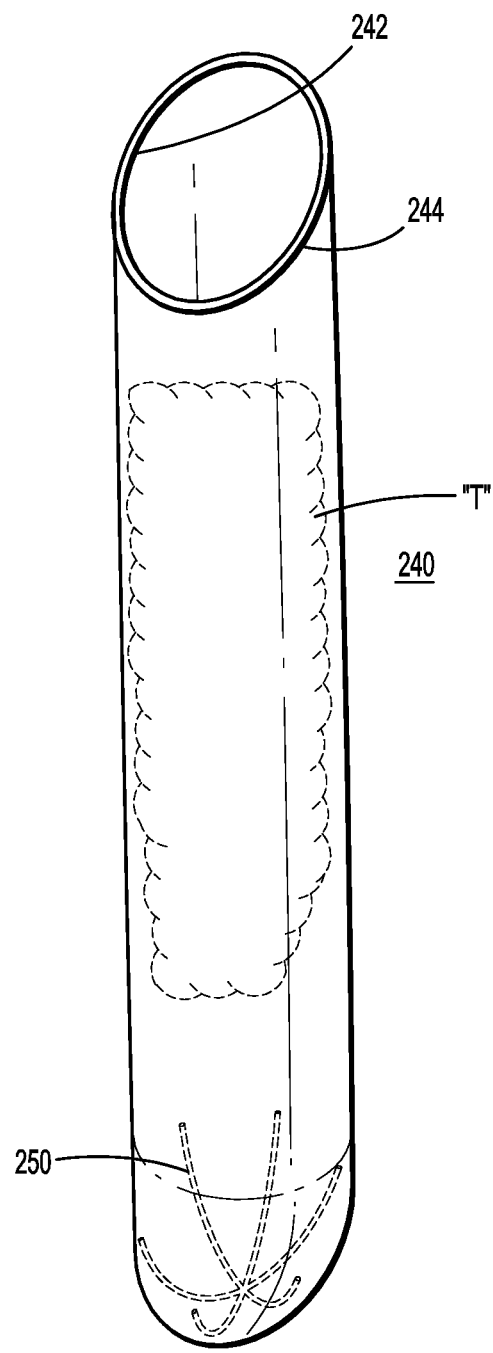
FIG. 13A is a perspective view of the specimen bag of FIG. 12, disposed in an expanded condition.
Figure 13B:
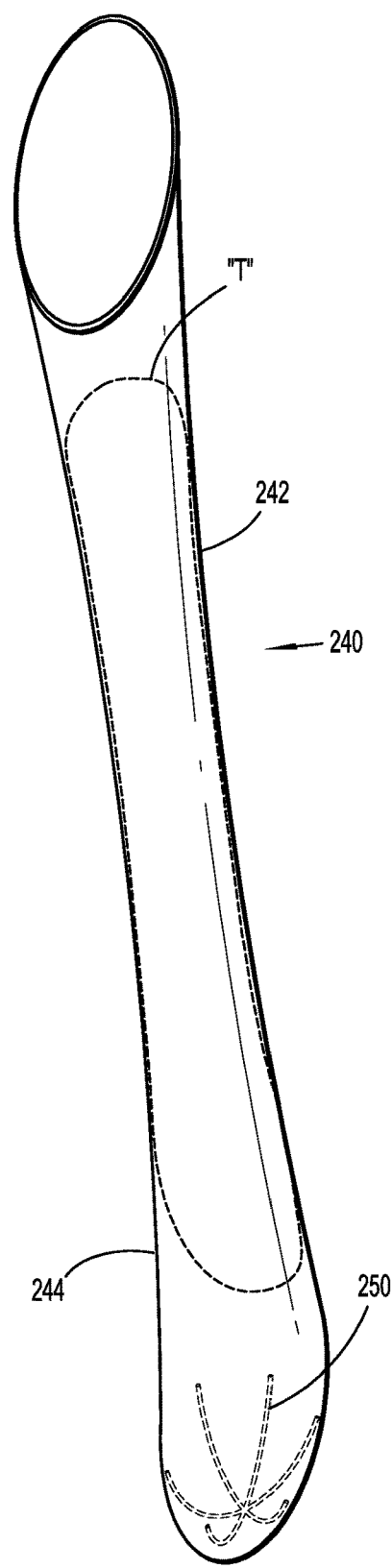
FIG. 13B is a perspective view of the specimen bag of FIG. 12, disposed in a contracted condition.

Referring to FIGS. 12, 13A, and 13B, still another specimen bag 240 configured for use with specimen retrieval device 10 (FIG. 1), any other suitable specimen retrieval device, or as a standalone specimen bag is shown. Specimen bag 240 may include any of the features of specimen bags 40, 140 (FIGS. 1-6 and 10-11, respectively) except that, rather than including ribs 60 and a pull string 62 as specimen bag 40 (see FIGS. 2-4) or a suction tube 160 as specimen bag 140 (FIGS. 10 and 11), specimen bag 240 includes a biaxial structure 242.

Specimen bag 240, more specifically, includes a biaxial structure 242 and a flexible bag body 244. An insert 250 may also be configured for use with specimen bag 240 for, as detailed below, maintaining at least a portion of specimen bag 240 in an expanded condition. Flexible bag body 244 may be formed from any suitable flexible and/or stretchable material capable of flexing and/or stretching in connection with manipulation of biaxial structure 242. Suitable materials include, for example, nylon. In embodiments, insert 250 may be replaced with insert 350 (FIG. 15) or both insert 250 and insert 350 (FIG. 15) may be utilized.

The biaxial structure 242 of specimen bag 240 may be a biaxial braid of material or other suitable structure biased to define a first length and a first diameter that, when a tension force, e.g., a longitudinal pulling force, is applied thereto, is compressed radially inwardly and elongated longitudinally to define a second length greater than the first length and a second diameter smaller than the first diameter. On the other hand, when a compression force, e.g., a longitudinal pushing forceps, is applied thereto, the biaxial structure 242 is expanded radially outwardly and compressed longitudinally to define a third length smaller than the first length and a third diameter greater than the first diameter. Biaxial structure 242 may be disposed externally of bag body 244, internally of bag body 244, or interposed between layers of material forming bag body 244, either entirely or partially, or any combination thereof.

Insert 250 may define a generally semi-spherical configuration or other suitable configuration and is formed from a plurality of fingers 254. Fingers 254 are attached to one another at a common end 252. Fingers 254 extend from common end 252 in an arcuate, spaced-apart manner to define the semi-spherical configuration of insert 250. Insert 250 may be monolithically formed from a single piece of material or the plurality of fingers 254 may be separately formed and then joined with one another, e.g., via welding at common end 252. Fingers 254 may be formed from nitinol or other suitable material providing sufficient structural strength to overcome the bias of biaxial structure 242 of specimen bag 240 to expand and maintain at least a portion of biaxial structure 242 in an increased-diameter configuration when insert 250 is disposed therein. The material forming fingers 254 is also sufficiently flexible to enable collapse for withdrawal, e.g., as specimen bag 240 is withdrawn into tubular body 12 (FIG. 1).

FIG. 13A illustrates specimen bag 240 in an expanded (radial) condition. Specimen bag 240 may be disposed in an at-rest condition, e.g., where no longitudinal force is applied thereto, to enable loading of tissue "T" therein, or a longitudinal pushing force may be applied to radially expand biaxial structure 242, thus enlarging the radial dimension of specimen bag 240, to enable loading of tissue "T" therein. In either configuration, insert 250 may be inserted into specimen bag 240 prior to loading of tissue "T" and positioned at the closed end of bag body 244 to maintain at least a portion of bag body 244 adjacent the closed end thereof in an expanded condition, thus facilitating loading of tissue "T" into specimen bag 240.

As shown in FIG. 13B, upon application of a longitudinal pulling force to specimen bag 240, e.g., to retract specimen bag 240 into tubular body 12 (FIG. 1), biaxial structure 242 is elongated and compressed radially inwardly to thereby compress bag body 244 and any tissue "T" within bag body 244 radially inwardly, reducing a transverse cross-sectional dimension of specimen bag 240 to facilitate removal from an internal surgical site. The longitudinal pulling force may be sufficient to collapse insert 250 inwardly to reduce the cross-sectional dimension thereof to facilitate removal. Alternatively, insert 250 may be removed from specimen bag 240 after loading of tissue "T" and prior to compression of specimen bag 240.

Figure 13C:
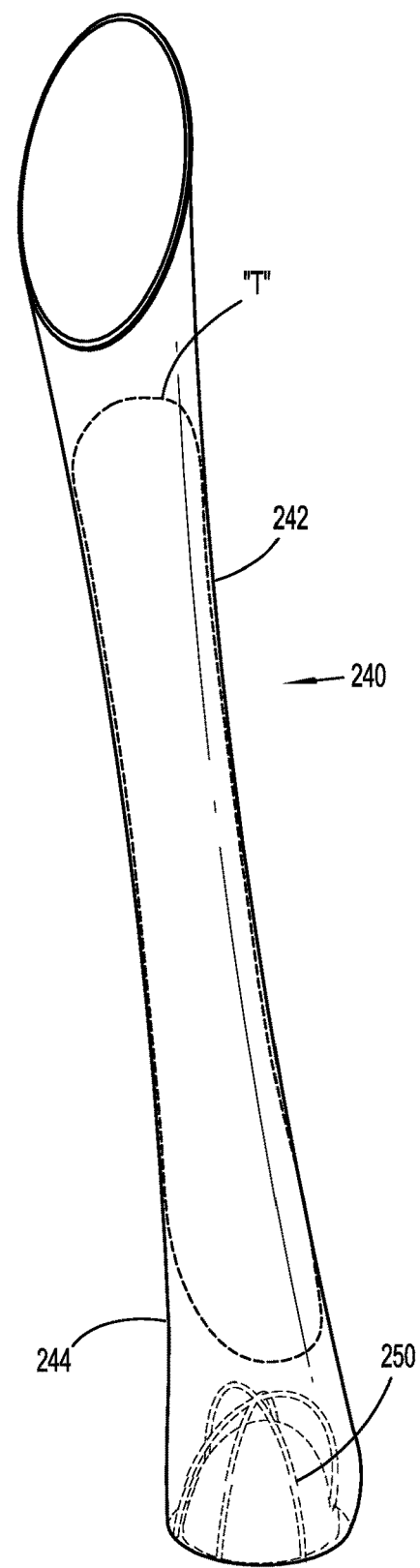
FIG. 13C is a perspective view of another configuration of the specimen bag of FIG. 12, disposed in the contracted condition.
Figure 14:
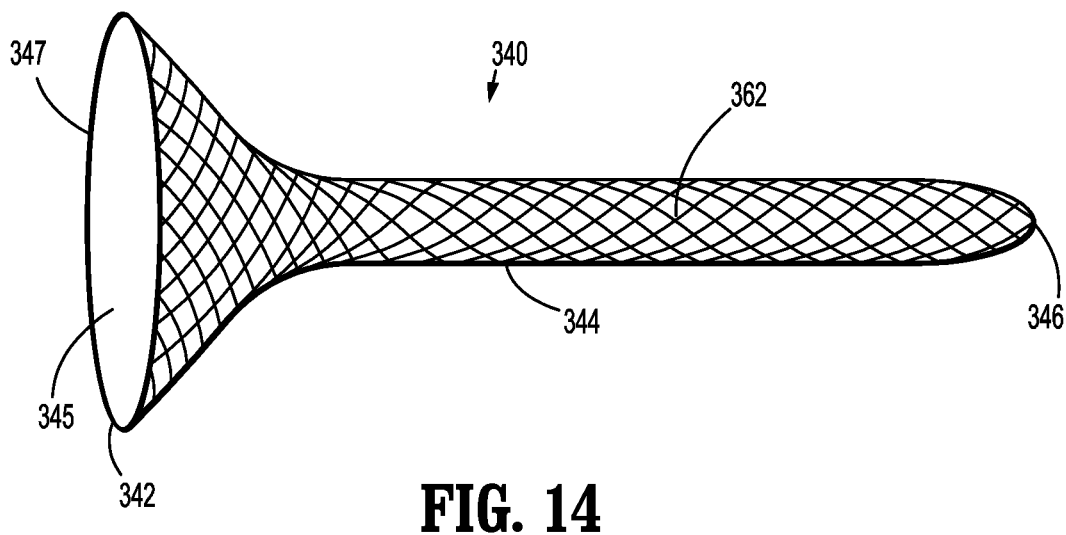
FIG. 14 is a side view of another specimen bag, disposed in a contracted condition.

As shown in FIGS. 13A and 13B, the closed end of bag body 244 defines a convex configuration and/or insert 250 is positioned within specimen bag 240 adjacent the closed end thereof in an orientation that maintains a convex configuration of the closed end of bag body 244. Alternatively, as shown in FIG. 13C, the closed end of bag body 244 may define a concave configuration and/or insert 250 may be positioned within specimen bag 240 adjacent the closed end thereof in an orientation that maintains a concave configuration of the closed end of bag body 244. Other configurations are also contemplated.

With reference to FIGS. 14-17 a specimen retrieval system 300 is provided including a specimen bag 340 and an insert 350. Initially referring to FIG. 14, specimen bag 340 includes a bag body 344 having a generally tubular, elongated sock-like configuration that is defined by an openable and closable mouth 342 and a closed end 346. Mouth 342 defines an opening 345 that may be opened and closed in any suitable manner, e.g., similarly as detailed above with respect to specimen bag 40 (FIGS. 2-4). Specimen bag 340 may be formed from any suitable material such as those detailed above with respect to specimen bag 40 (FIGS. 2-4).

Specimen bag 340 includes a biaxial structure 362, e.g., a biaxial braid of material or other suitable structure, biased towards a compressed configuration defining a minimum diameter and a maximum length. When a radially outward force sufficient to overcome the bias of biaxial structure 362, e.g., provided by insert 350, as detailed below, is applied to biaxial structure 362, biaxial structure 362 is expanded radially outwardly to define an increased diameter and is contracted longitudinally to define a reduced length. Upon removal of the force sufficient to overcome the bias, biaxial structure 362 is returned towards the compressed configuration defining the minimum diameter and maximum length.

Biaxial structure 362 may be disposed externally of bag body 344 of specimen bag 340, internally of bag body 344 or interposed between layers of material forming bag body 344, either entirely or partially, or any combination thereof.

Specimen bag 340 may further include a reinforcement ring 347, e.g., formed from nitinol or other suitable material, disposed about mouth 342 of specimen bag 340 to maintain mouth 342 and, thus, opening 345, in an open condition regardless of the condition of biaxial structure 362. Reinforcement ring 347, in embodiments, may itself be collapsible, removable, or otherwise configured to enable selective closure of mouth 342, e.g., to enclose tissue within specimen bag 340.

Figure 15:
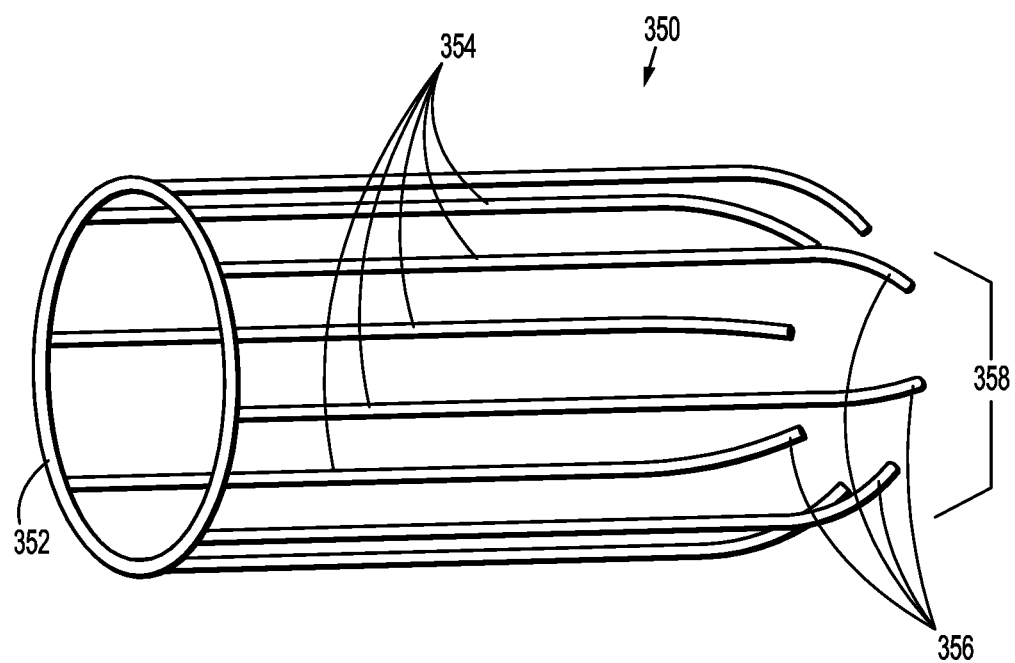
FIG. 15 is a side view of an insert configured for use with the specimen bag of FIG. 14.

Referring to FIG. 15, insert 350 includes a base ring 352 and a plurality of fingers 354 attached to base ring 352 at positioned spaced-apart about the circumference of base ring 352 and extending axially from base ring 352 such that insert 350 defines a generally tubular structure. Notwithstanding the generally tubular structure of insert 350, free ends 356 of fingers 354 are curved, angled, or otherwise directed inwardly to define a generally conical-shaped tip portion 358 of insert 350. Insert 350 may be monolithically formed from a single piece of material or base ring 352 and the plurality of fingers 354 may be separately formed and then joined with one another, e.g., via welding. Base ring 352 and the plurality of fingers 354 may be formed from the same material, e.g., nitinol, or may be formed from different materials. Fingers 354 define sufficient structural strength to overcome the bias of biaxial structure 362 of specimen bag 340 to expand and maintain biaxial structure 342 in the increased diameter, reduced length configuration when insert 350 is inserted therethrough. In embodiments, insert 350 may be replaced with insert 250 (FIG. 12) or both insert 350 and insert 250 (FIG. 12) may be utilized.

Figure 16:
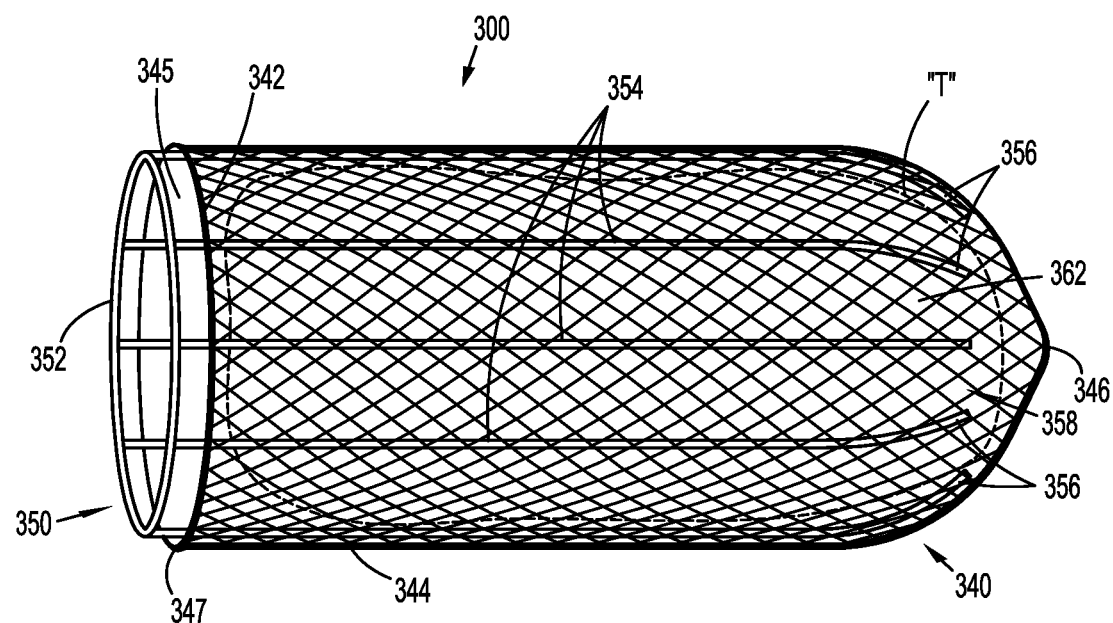
FIG. 16 is a side view illustrating the insert of FIG. 15 disposed within the specimen bag of FIG. 14 to retain the specimen bag in an expanded condition.

FIG. 16 illustrates insert 350, led by conical-shaped tip portion 358, disposed within bag body 344 of specimen bag 340 to maintain biaxial structure 342 in the increased diameter, reduced length configuration, thereby maintaining specimen bag 340 in an expanded condition that generally approximates the diameter of the generally tubular insert 350. Conical-shaped tip portion 358 of insert 350 facilitates insertion of insert 350 into bag body 344 and also at least partially conforms with the contour of closed end 346 of bag body 344 when insert 350 is fully received within bag body 344.

With insert 350 maintaining specimen bag 340 in an expanded condition, tissue "T" can be more easily loaded through mouth 342 and into bag body 344. Tissue "T," more specifically, is inserted through base ring 352 and the generally tubular structure of insert 350 such that tissue "T" is surrounded by fingers 354.

Figure 17:
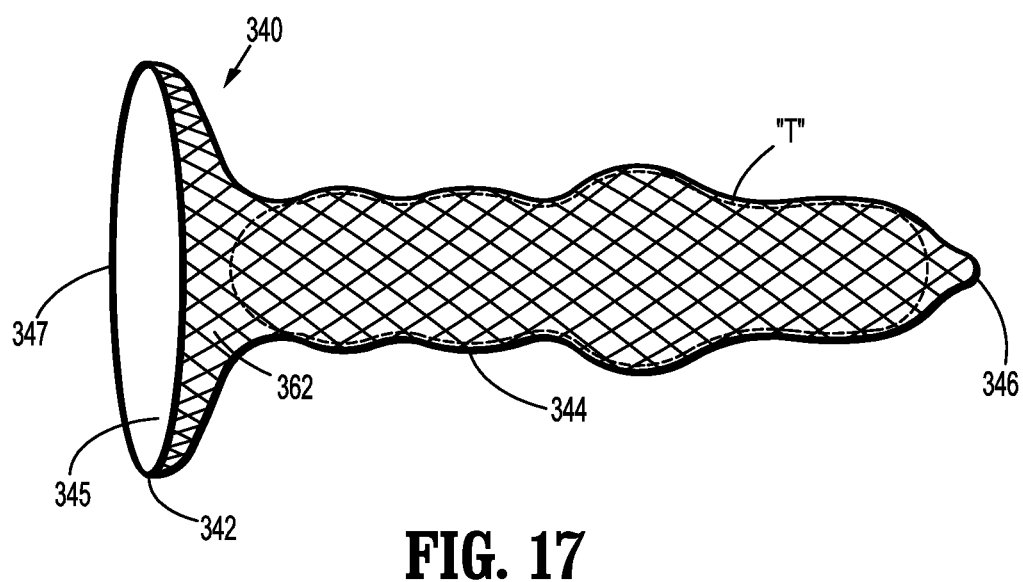
FIG. 17 is a side view of the specimen bag of FIG. 14 in the contracted condition retaining tissue therein.

Referring to FIG. 17, once tissue "T" is positioned within bag body 344, insert 350 may be withdrawn from bag body 344 through mouth 342 (and about tissue "T"), allowing biaxial structure 362 to return, under its bias, back towards the compressed configuration, wherein biaxial structure 362 compresses tissue "T" to reduce the transverse diameter thereof (as well as the transverse diameter of specimen bag 340).

FIGS. 18-21 illustrate another specimen retrieval system 400. Specimen retrieval system 400 includes a frame assembly (formed from a plurality of rods 412 and/or other suitable structures) and a plurality of collars 420 and may be utilized to facilitate removal of a specimen, e.g., tissue "T," enclosed within a specimen bag 440 from an internal surgical site. In embodiments, specimen bag 440 is included as part of specimen retrieval system 400; in other embodiments, specimen bag 440 is separate therefrom enabling use of specimen retrieval system 400 with any other suitable specimen bag or without a specimen bag.

With initial reference to FIG. 18, the frame assembly, in embodiments, includes at least three rods 412. Each rod defines a stop 414 at a distal end thereof. Stop 414 may be in the form of a turned-out distal tip, as illustrated, an outwardly-extending protrusion, or other suitable stop 414 to inhibit collars 420 from sliding distally off of rods 412.

Referring also to FIG. 19, each collar 420 is substantially similar and includes a disc-shaped body 422 defining a plurality of radially-arranged slots 424 extending longitudinally therethrough and a central opening 426 extending longitudinally therethrough. Central opening 426 may define a triangular transverse cross-sectional configuration or any other suitable configuration, e.g., other polygon, circle, oval, etc. In embodiments where central opening 426 defines a triangular transverse cross-sectional configuration, three radially-arranged slots 424 may be provided each in general alignment with one of the sides of the triangular central opening 426, as illustrated in FIG. 19. Each slot 424 is configured to receive one or more of the rods 412 therethrough to enable the collars 420 to slide longitudinally about the rods 412, as detailed below.

Turning back to FIG. 18, in use, specimen bag 440 is deployed within an internal surgical site and a specimen, e.g., tissue "T," is loaded into specimen bag 440. Specimen bag 440 is then closed to retain tissue "T" therein. In order to remove specimen bag 440, together with tissue "T" therein, from the internal surgical site, rods 412, led by the distal ends thereof, are inserted into the internal surgical site and arranged to define a passageway extending longitudinally through the frame assembly. With rods 412 positioned in this manner, a first collar 420 of the plurality of collars 420 is inserted over the proximal ends of rods 412, with each rod 412 received within one of the slots 424 of the first collar 420. Thereafter, first collar 420 is slid distally about rods 412 into the internal surgical site. First collar 420 is moved distally towards or to stops 414, which inhibit further distal sliding of first collar 420 and retain first collar 420 on rods 412.

Figure 20:
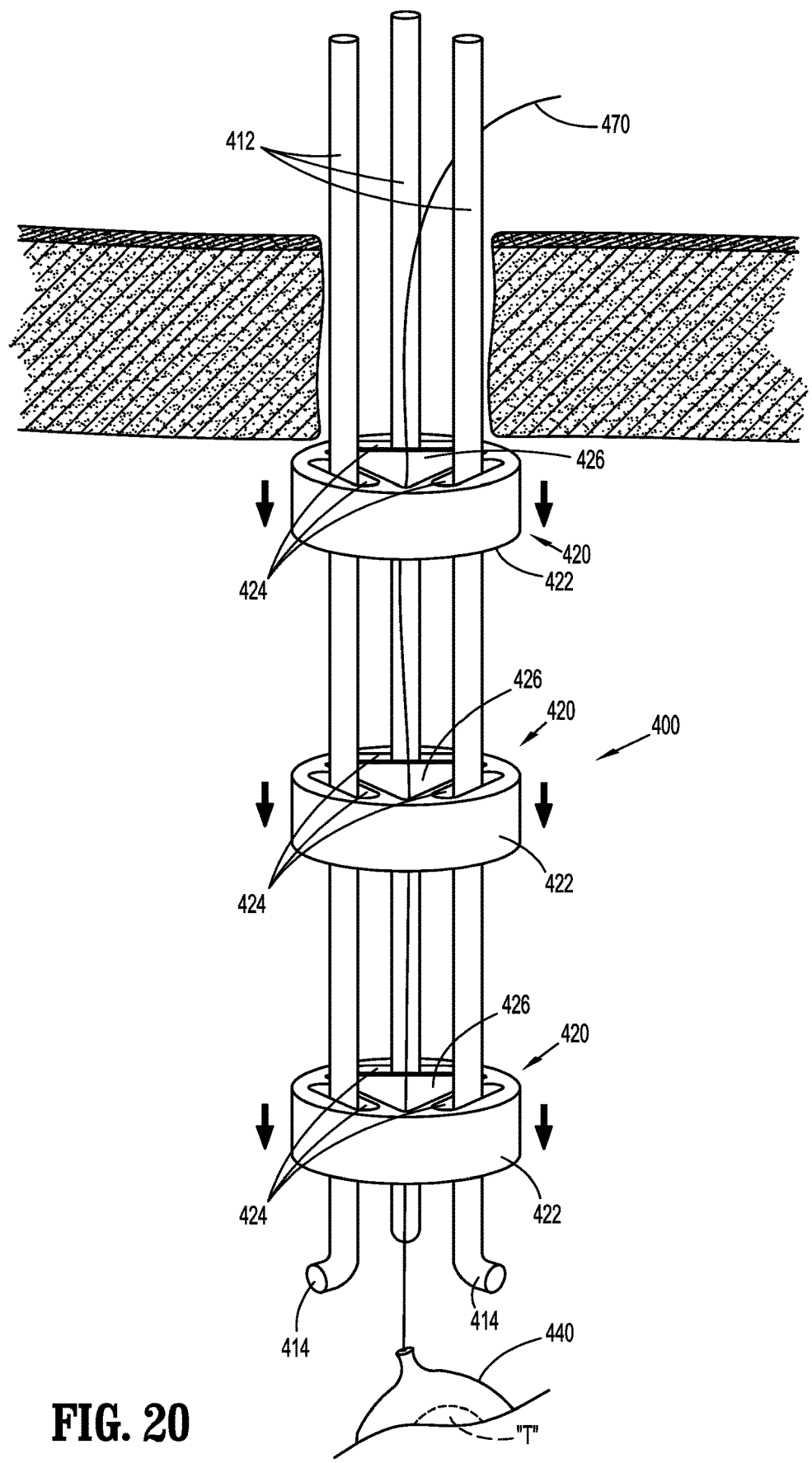
FIGS. 20 and 21 are perspective views progressively illustrating the specimen retrieval device of FIG. 18 in use removing tissue from the internal body cavity.

Referring to FIG. 20, subsequent collars 420 are inserted about and slid distally about rods 412 similarly as detailed above with respect to the first collar 420. The plurality of collars 420 may be positioned at longitudinally-spaced positions relative to one another or in any other suitable configuration. Although three collars 420 are illustrated, greater or fewer collars 420 may be provided.

Figure 21:
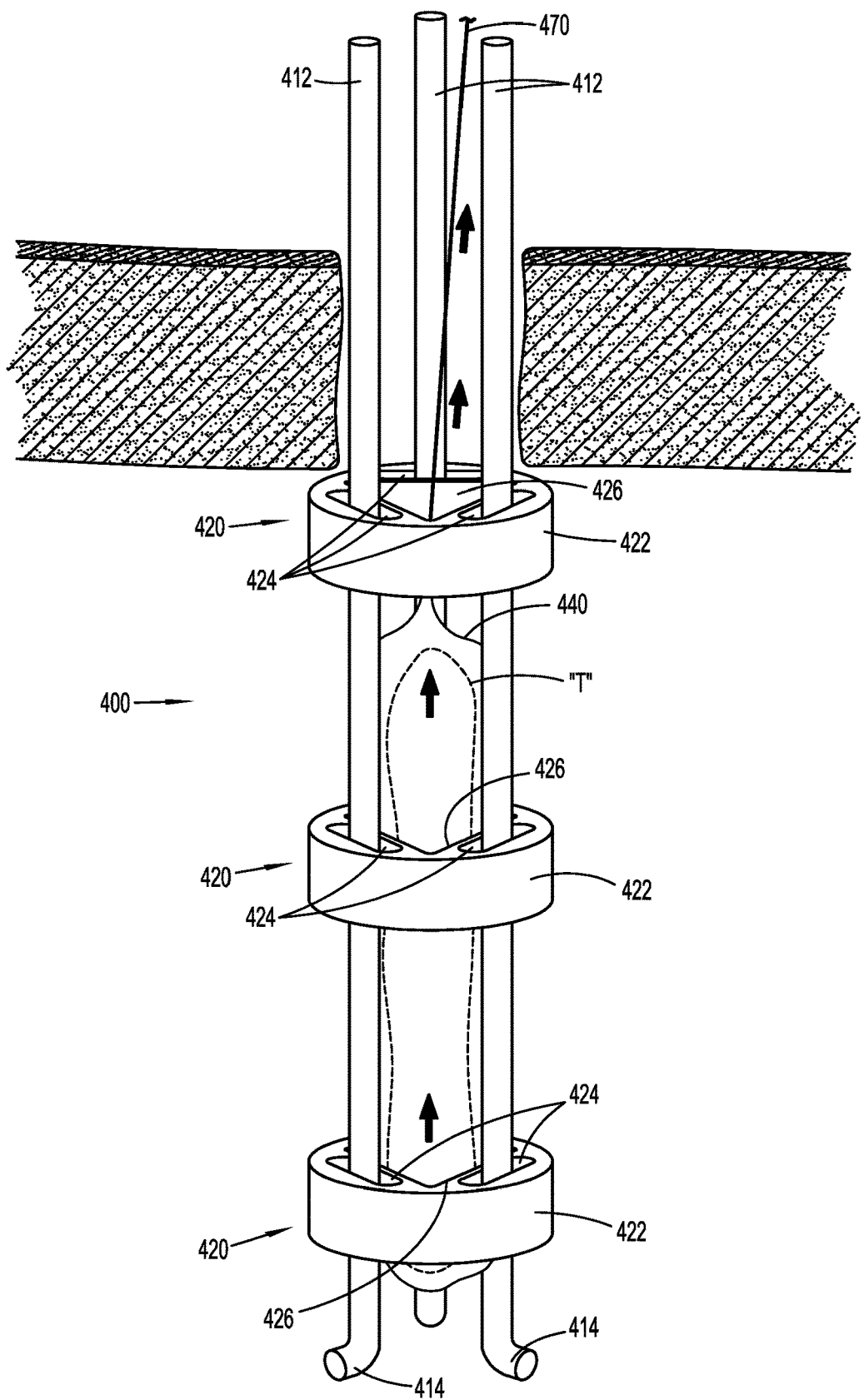

Collars 420 serve to stabilize rods 412 and maintain a passageway therethrough for removal of specimen bag 440 and tissue "T" therein. Central openings 426 of collars 420 are disposed within the passageway defined by rods 412 and enable specimen bag 440 and tissue "T" therein to pass therethrough while functioning to compress and reduce the transverse dimension thereof. More specifically, as shown in FIG. 21, in order to remove specimen bag 440 and tissue "T" therein from the internal surgical site, a pull string 470 associated with specimen bag 440 is grasped and pulled through the passageway defined by rods 412 as well as the central opening 426 of each collar 420 disposed about rods 412.

Pull string 470, once routed through rods 412 and collars 420, is pulled proximally to draw specimen bag 440 and the tissue "T" therein proximally through the passageway defined by rods 412 and the central opening 426 of each successive collar 420 disposed about rods 412. In this manner, specimen bag 440 and the tissue "T" therein are compressed by rods 412 and collars 420 to facilitate withdrawal from the internal surgical site. As specimen bag 440 and the tissue "T" therein are pulled through the passageway defined by rods 412 and the central openings 426 of collars 420, rods 412 are permitted to slide transversely through slots 424 to provide compliance to the frame assembly thereby facilitating passage of specimen bag 440 and the tissue "T through the frame assembly and inhibit snags, damage to the frame assembly, damage to specimen bag 440, etc.

FIGS. 22-25 illustrate still another specimen retrieval system 500. Specimen retrieval system 500 includes a tube 510, a connector assembly 520, and a specimen bag 540 and is configured to connect to a source of pressure and suction 550 (although separate pressure and suction sources are also contemplated).

Figure 22:
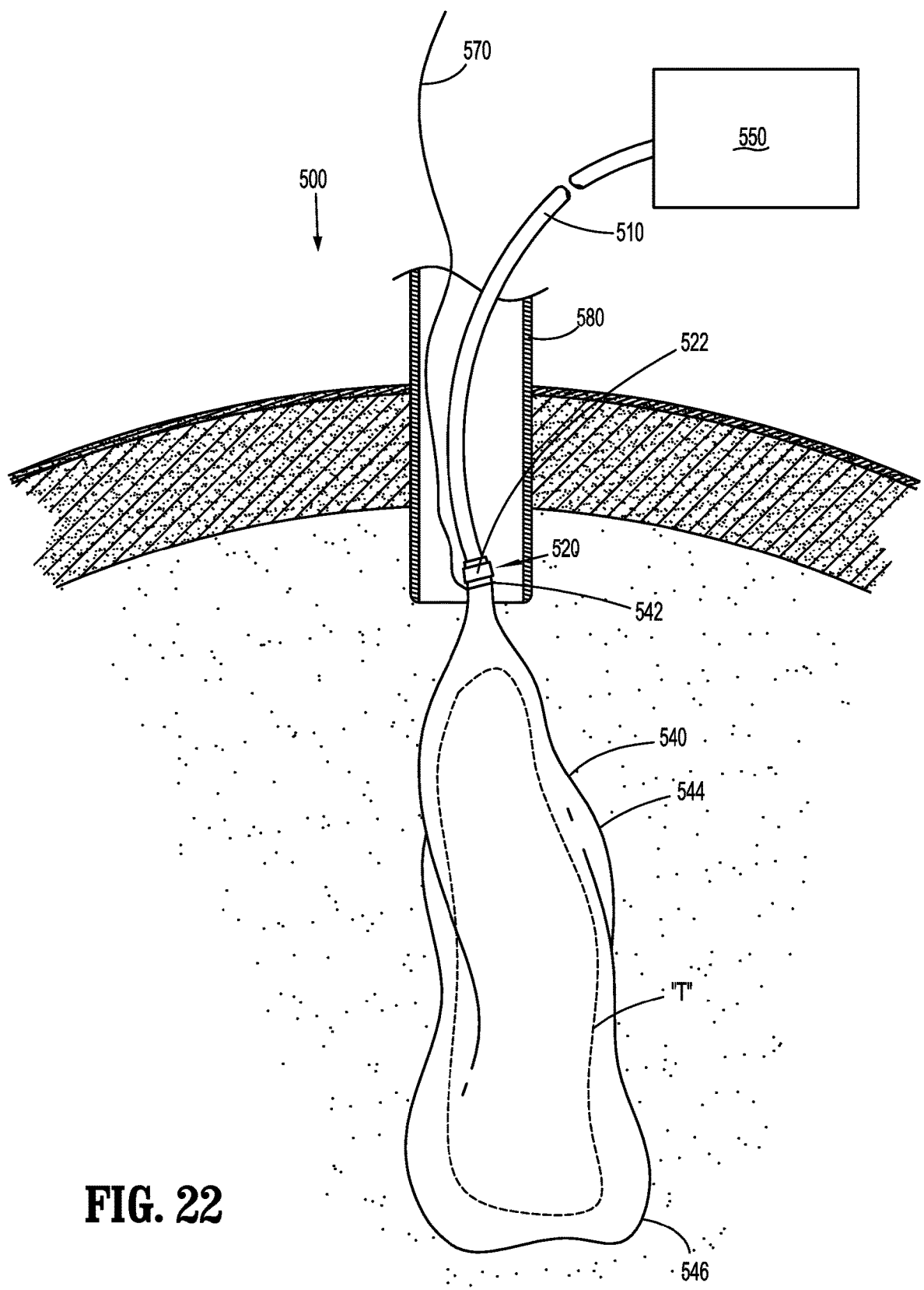
FIG. 22 is a side view of a specimen retrieval system in use within an internal body cavity.

Referring initially to FIG. 22, specimen bag 540 includes a bag body 544 having a generally tubular, elongated sock-like configuration that is defined by an openable and closable mouth 542 and a closed end 546. Specimen bag 540 may be formed from any suitable material such as those detailed above with respect to specimen bag 40 (FIGS. 2-4). Specimen bag 540 further includes a pull string 570 engaged or engagable about mouth 542 to facilitate manipulation of specimen bag 540.

Tube 510 is configured to operably couple to the source of pressure and suction 550 at a proximal end thereof and to connector assembly 520 at a distal end thereof. Connector assembly 520 may be disposed on the distal end of tube 510, about mouth 542 of specimen bag 540, or may include some components disposed on the distal end of tube 510 and other components disposed about mouth 542 of specimen bag 540. Connector assembly 520 (and/or the portions thereof) may be permanently associated with the distal end of tube 510 and/or mouth 542 of specimen bag 540 or may be removable therefrom.

Connector assembly 520 enables coupling of the distal end of tube 510 with mouth 542 of specimen bag 540 in sealed relation to inhibit the escape of fluid at the coupling. Connector assembly 520, in embodiments, includes a ring 522 disposed about tube 510 towards the distal end thereof that, upon positioning of the distal end of tube 510 within mouth 542 of specimen bag 540, is configured to move, e.g., slide or roll, distally for positioning about mouth 542 of specimen bag 540 to retain mouth 542 of specimen bag 540 about the exterior surface of tube 510 in sealed relation therewith. Ring 522 may be formed from a resilient material, e.g., an elastomer, to maintain the seal under resilient compression; may be configured for mechanically-adjustment, e.g., as a cable-tie, belt, etc., to enable constriction sufficient to maintain the seal under mechanical engagement; or may define any other suitable configuration.

Alternatively, mouth 542 of specimen bag 540 may be cinched or otherwise closed and connector assembly 520 may be configured to connect tube 510 to the interior of specimen bag 540 through a sidewall thereof. In such embodiments, connector assembly 520 may include complementary connectors disposed on the distal end of tube 510 and within an opening in the sidewall of specimen bag 540 to enable releasable sealed engagement therebetween.

Regardless of the particular manner of connecting tube 510 and specimen bag 540 with one another, the connection therebetween, e.g., via connection assembly 520, enables the pumping of fluid through tube 510 into specimen bag 540 and/or the withdrawal of fluid out of specimen bag 540 through tube 510 to facilitate withdrawal of a specimen, e.g., tissue "T," from an internal surgical site.

Figure 24:
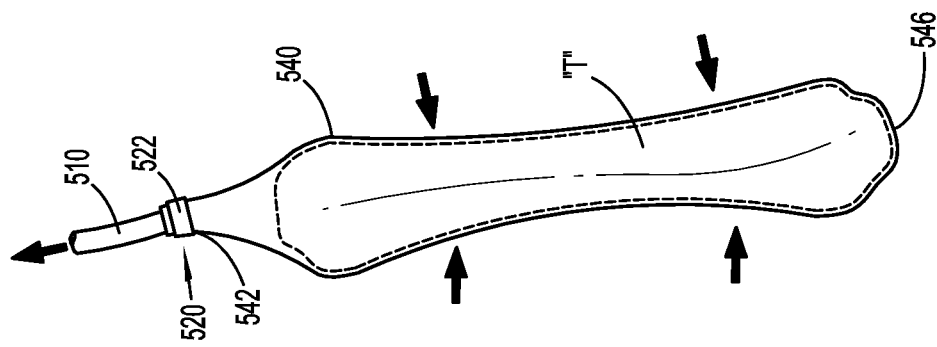
FIG. 24 is an enlarged, perspective view of the specimen bag of the specimen retrieval system of FIG. 22, disposed in a contracted condition.
Figure 23:
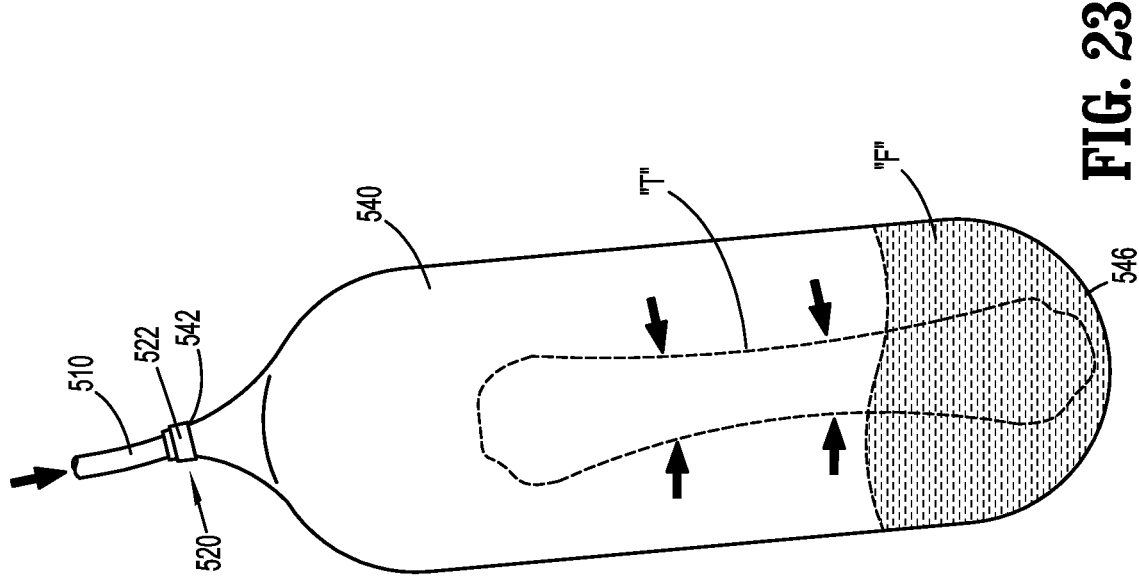
FIG. 23 is an enlarged, perspective view of a specimen bag of the specimen retrieval system of FIG. 22, disposed in an expanded condition.
Figure 25:
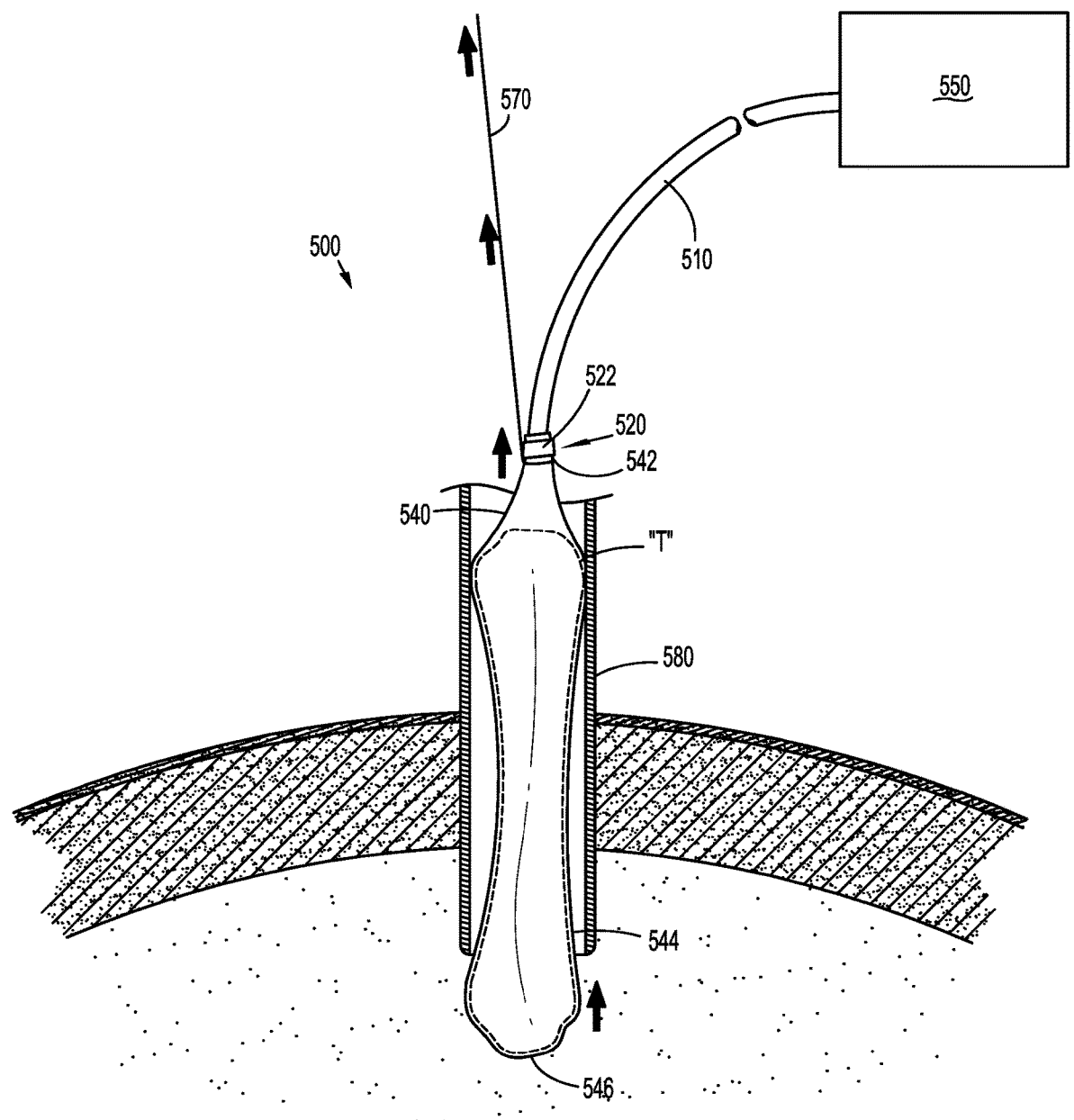
FIG. 25 is a side view illustrating the specimen retrieval system of FIG. 22 in use removing tissue from the internal body cavity.

More specifically, with reference to FIGS. 23-25, in use, specimen bag 540 is initially deployed within an internal surgical site and a specimen, e.g., tissue "T," is loaded into specimen bag 540. Connector assembly 520 is then utilized to connect tube 510 with specimen bag 540. As illustrated in FIG. 23, once connection is made, the source of pressure and suction 550 (FIG. 22) is activated in a pressure mode to pump fluid, e.g., air, through tube 510 and into specimen bag 540 to pressurize specimen bag 540 and tissue "T" therein. As a result, tissue "T" is compressed such that fluids "F," e.g., blood, water, etc., is squeezed out of tissue "T," reducing the volume of tissue "T."

Referring to FIG. 24, once the fluids "F" are squeezed out and/or the volume of tissue "T" is sufficiently reduced, the source of pressure and suction 550 (FIG. 22) is reversed and activated in a suction mode to remove the fluid "F" from specimen bag 540 through tube 510, leaving behind the reduced-volume tissue "T" in specimen bag 540.

The above-detailed application of pressure (FIG. 23) to pump fluid into the specimen bag, pressurize the specimen bag, and squeeze fluids out of tissue disposed within the specimen bag, followed by application of suction (FIG. 24) to remove the fluid, thereby reducing the volume of tissue within the specimen bag may, to the extent consistent, be utilized with any or all of the embodiments detailed herein to facilitate removal.

Next, as illustrated in FIG. 25, specimen bag 540, including the reduced-volume tissue "T" therein, can be removed from the surgical site, e.g., through an access port 580 or in any other suitable manner, using pull string 570.

In embodiments, rather than pumping fluid directly into specimen bag 540 to compress tissue "T" to squeeze fluids "F" therefrom, an outer balloon (not shown) formed from a relatively stiff material may be disposed about specimen bag 540 (e.g., integrated therewith, disposed thereabout prior to insertion, or disposed thereabout after insertion) and inflated to compress specimen bag 540 and tissue "T" therein to squeeze fluids "F" from tissue "T." Further, other suitable compression mechanisms such as mechanical compression mechanisms may be utilized to squeeze the fluids "F" from tissue "T" to reduce the volume of tissue "T" thus facilitating removal.

Figure 26:
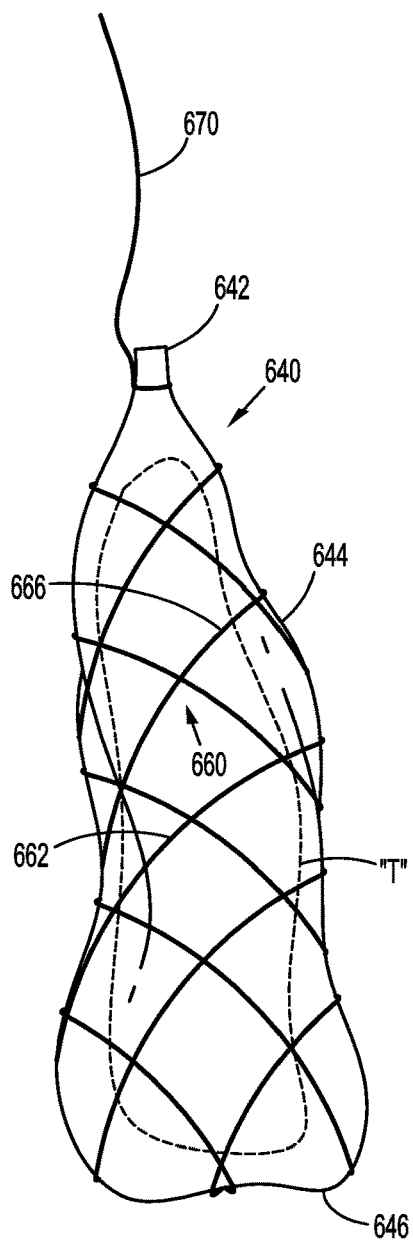
FIG. 26 is a perspective view of yet another specimen bag configured for use with the specimen retrieval device of FIG. 1, any other suitable specimen retrieval device, or as a standalone specimen bag, disposed in an expanded condition.
Figure 27:
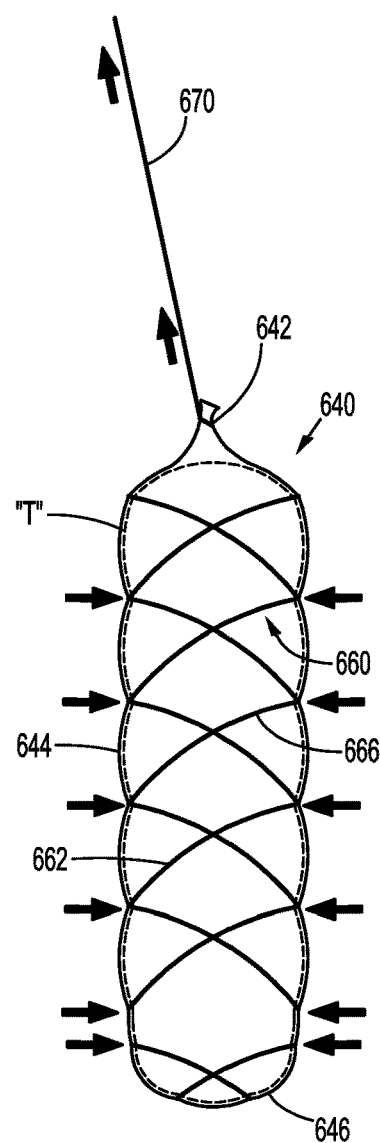
FIG. 27 is a perspective view of the specimen bag of FIG. 26, disposed in a contracted condition.

With reference to FIGS. 26 and 27, still another specimen bag 640 configured for use with specimen retrieval device 10 (FIG. 1), any other suitable specimen retrieval device, or as a standalone specimen bag is shown. Specimen bag 640 may include any of the features of specimen bags 40, 140, 240 (FIGS. 1-6, 10-11, and 12-13, respectively) except that, rather than including ribs 60 and a pull string 62 as specimen bag 40 (see FIGS. 2-4), a suction tube 160 as specimen bag 140 (FIGS. 10 and 11), or a biaxial structure 242 as specimen bag 240 (FIGS. 12 and 13), specimen bag 640 includes a tie arrangement 660 forming a netting 662.

Tie arrangement 660 may be disposed externally of bag body 644 of specimen bag 640, internally of bag body 644 or interposed between layers of material forming bag body 644, either entirely or partially, or any combination thereof. Tie arrangement 660 includes one or more strands 666 of suture, wire, string, etc., disposed about bag body 644 to define netting 662. Netting 662 extends about the periphery of bag body 644, closed end 646 of bag body 644, and a substantial portion of a length of bag body 644. A pull string 670, e.g., an extension of one of the strands 666 or a separate string, is attached to tie arrangement 660. The strands 666 of tie arrangement 660 are arranged such that, upon proximal pulling of pull string 670, netting 662 is contracted, thereby constricting bag body 644 of specimen bag 640 and anything therein, e.g., tissue "T" (see FIG. 27). This may be accomplished, for example, by intertwining, providing one or more separate helixes, or otherwise arranging strands 666.

In use, with reference to FIG. 26, specimen bag 640 is initially deployed within an internal surgical site and a specimen, e.g., tissue "T," is loaded into specimen bag 640. Mouth 642 of specimen bag 640 is then closed to retain the tissue "T" within specimen bag 640. In order to retrieve specimen bag 640, with tissue "T" therein, from the internal surgical site, pull string 670 is pulled proximally.

As shown in FIG. 27, proximal pulling of pull string 670 not only pulls specimen bag 640 proximally but also contracts netting 662, thereby constricting bag body 644 of specimen bag 640 and tissue "T" therein to define a reduced transverse cross-sectional dimension, thus facilitating withdrawal from the internal surgical site.

Figure 28:
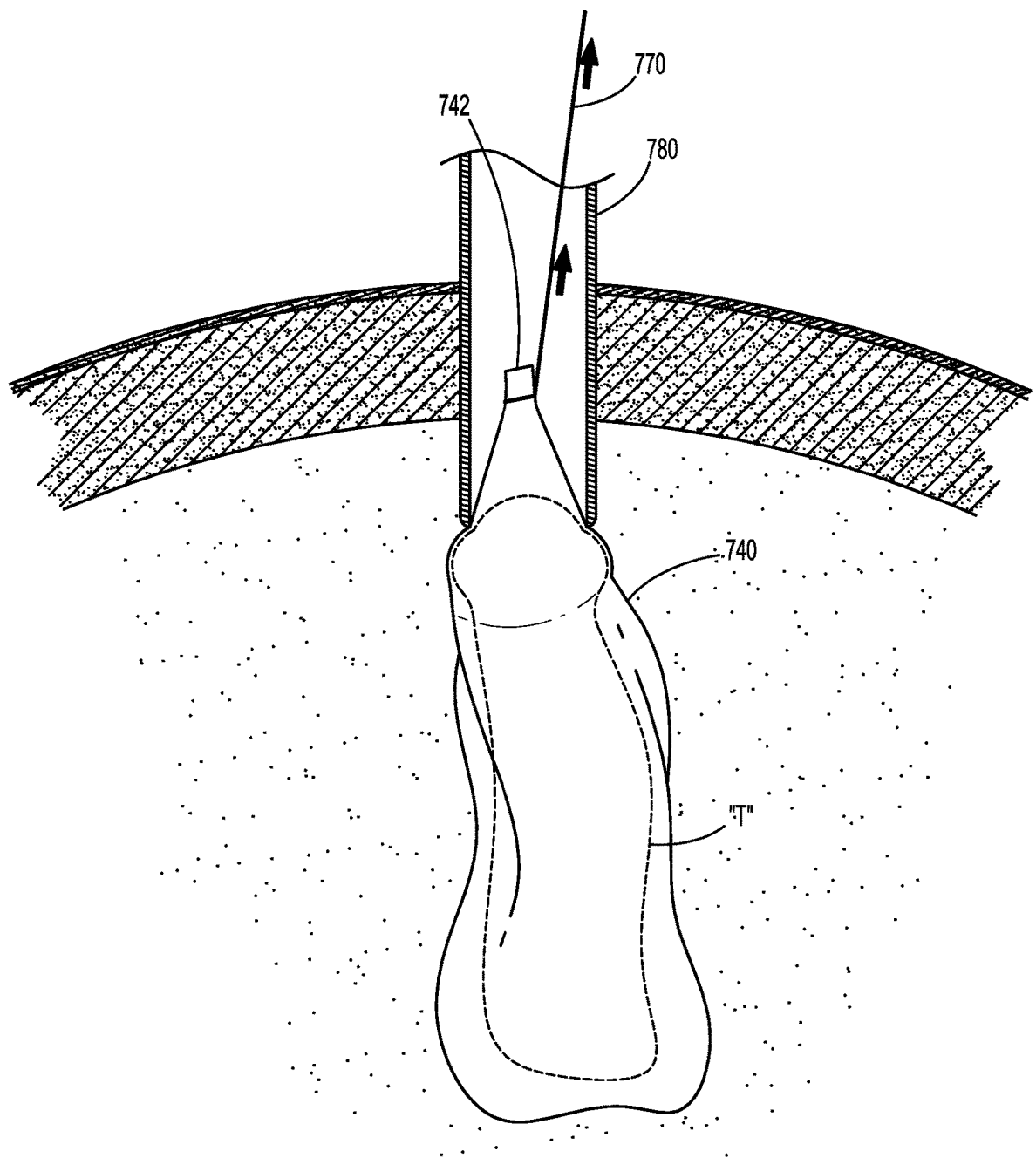
FIG. 28 is a side view illustrating removal of tissue disposed within a specimen bag in a first manner.
Figure 29:
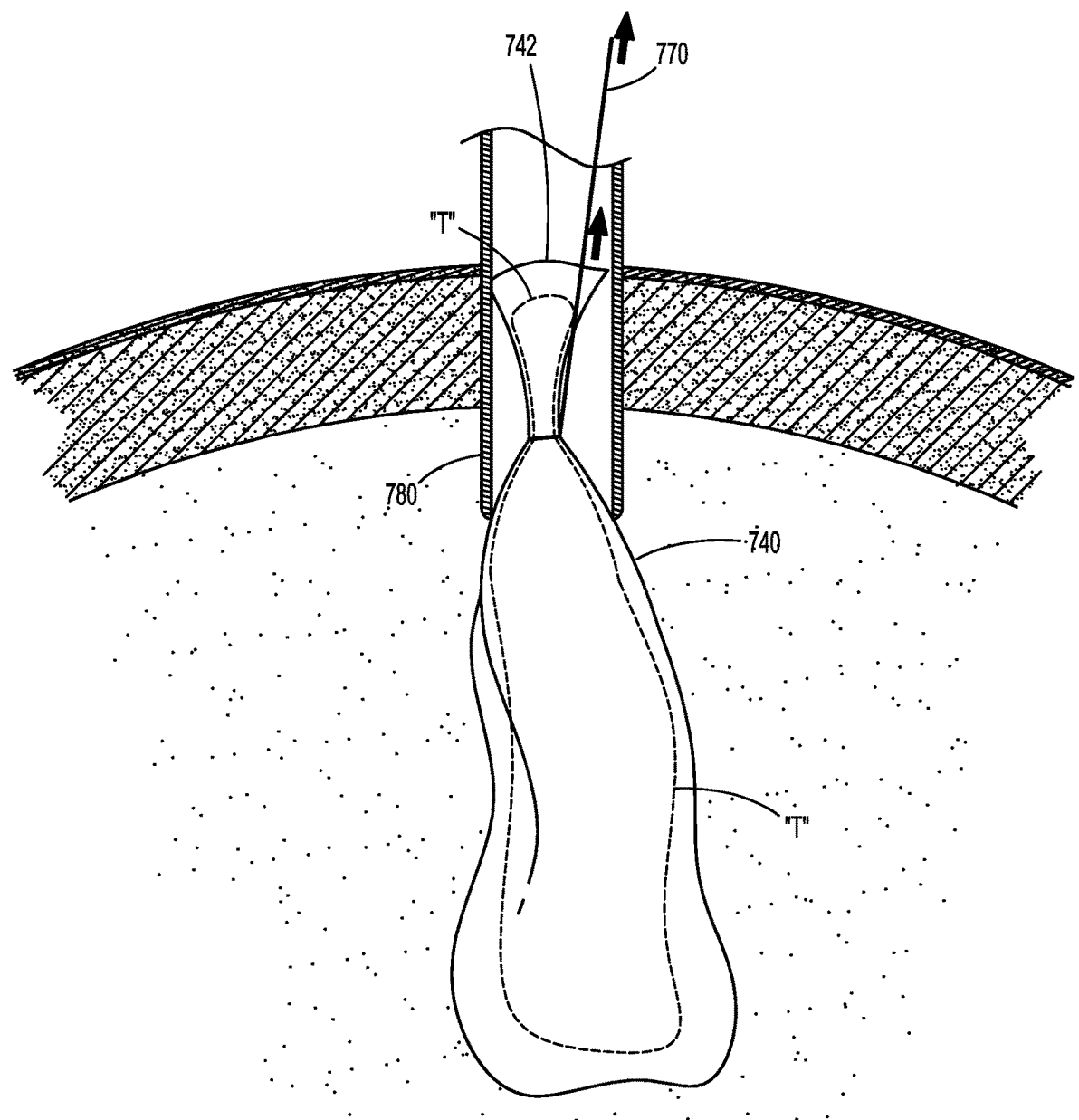
FIG. 29 is a side view illustrating removal of tissue disposed within a specimen bag in a second, different manner.
Figure 30:
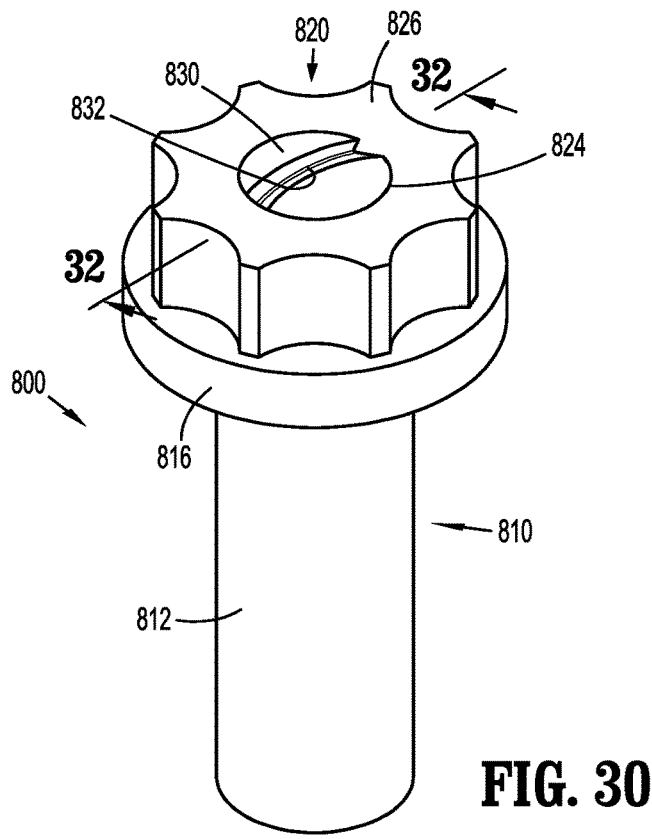
FIG. 30 is a perspective view of a cannula assembly configured to facilitate withdrawal of a tissue containing specimen bag therethrough.
Figure 31:
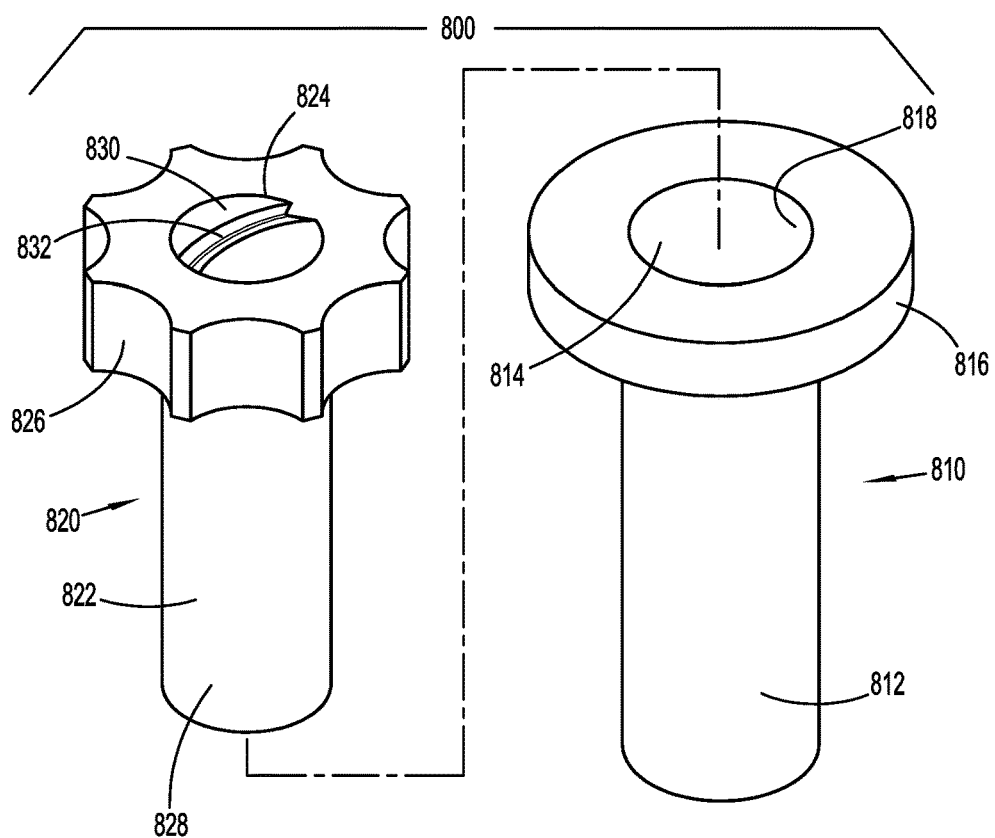
FIG. 31 is a perspective view, with parts separated, of the cannula assembly of FIG. 30.

Referring to FIGS. 28 and 29, and initially with reference to FIG. 28, it has been found that attaching or tightening a pull string 770 about a specimen bag 740 in a manner such that the pull string 770 surrounds a portion of the specimen bag 740 not occupied by tissue "T" may lead to bunching of the tissue "T" at a distal opening of an access device 780 as pull string 770 pulls the mouth 742 of the specimen bag 740 therethrough. This bunching may increase resistance and make removal of the specimen bag 740 more difficult.

Accordingly, as illustrated in FIG. 29, in order to alleviate or at least reduce the bunching of tissue, the pull string 770 may be attached or tightened about a portion of specimen bag 740 that includes tissue "T" disposed therein. Thus, the pull string 770 not only grasps the specimen bag 740 but also grasps the tissue "T" therein. As a result, when pull string 770 is pulled proximally, both the specimen bag 740 and the tissue "T" are pulled proximally, thereby reducing bunching and facilitating drawing the specimen bag 740 and the tissue "T" through the distal opening of the access device 780.

With reference to FIGS. 30-33, yet another specimen retrieval system 800 is shown. Specimen retrieval system 800 includes an outer cannula 810 and an inner cannula 820 and may be utilized to facilitate removal of a specimen, e.g., tissue "T," enclosed within a specimen bag 840 from an internal surgical site. In embodiments, specimen bag 840 is included as part of specimen retrieval system 800; in other embodiments, specimen bag 840 is separate therefrom enabling use of specimen retrieval system 800 with any other suitable specimen bag or without a specimen bag.

Outer cannula 810 includes a tubular body 812 defining a longitudinal passageway 814 extending therethrough and a proximal hub 816 disposed at the proximal end of tubular body 812. Tubular body 812 is configured for insertion through an opening in tissue and into an internal surgical site while proximal hub 816 is configured to be position adjacent or in abutment with an external surface of tissue, e.g., surrounding the opening in tissue.

Inner cannula 820 includes a tubular body 822 defining a longitudinal passageway 824 extending therethrough and a proximal hub 826 disposed at the proximal end of tubular body 822. Tubular body 822 is configured for insertion through longitudinal passageway 814 of tubular body 812 of outer cannula 810 and into an internal surgical site. Proximal hub 826 is configured for positioning atop proximal hub 816 of outer cannula 810.

An interior surface 818 of tubular body 812 of outer cannula 810, e.g., defining longitudinal passageway 814, and an exterior surface 828 of tubular body 822 of inner cannula 820 may both be smooth to facilitate rotation of inner cannula 820 within and relative to outer cannula 810. Additionally or alternatively, one or both surfaces 818, 828 may be lubricated and/or include other features to facilitate rotation of inner cannula 820 within and relative to outer cannula 810.

An interior surface 830 of tubular body 822 of inner cannula 820, e.g., defining longitudinal passageway 824, includes threading 832 defined thereon and/or disposed thereon. That is, threading 832 may protrude inwardly from interior surface 830 and/or be recessed into interior surface 830. Threading 832 is pitched in either a clockwise or counterclockwise direction.

Figure 32:
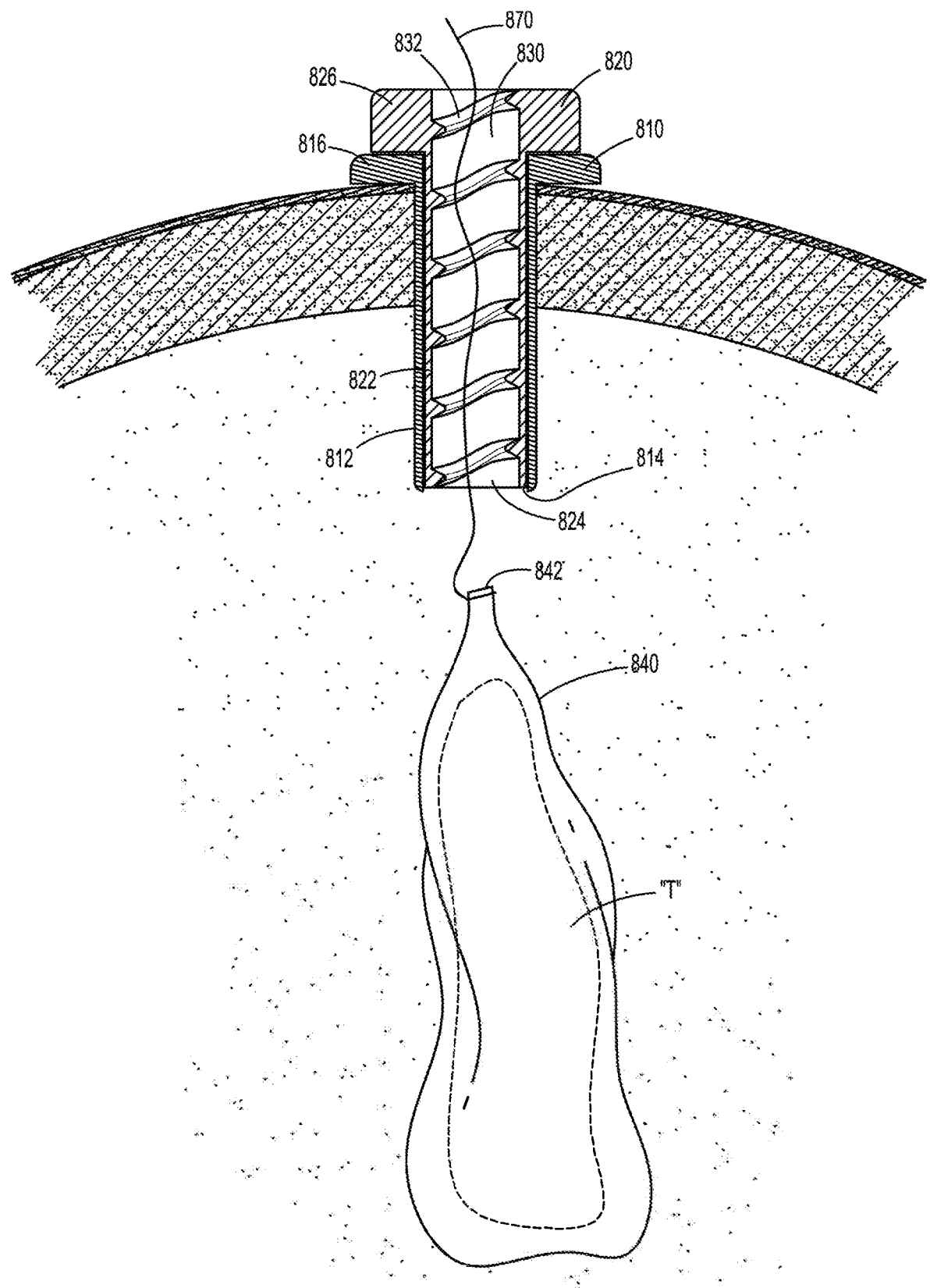
FIGS. 32 and 33 are partial cross-sectional views progressively illustrating withdrawal of the tissue containing specimen bag through the cannula assembly of FIG. 30.

Continuing with reference to FIG. 32, in use, specimen bag 840 is initially deployed within an internal surgical site and a specimen, e.g., tissue "T," is loaded into specimen bag 840. Mouth 842 of specimen bag 840 is then closed to retain the tissue "T" within specimen bag 840. After, or prior to the above, outer cannula 810 is inserted through an opening in tissue and into the internal surgical site and inner cannula 820 is inserted into outer cannula 810.

Figure 33:
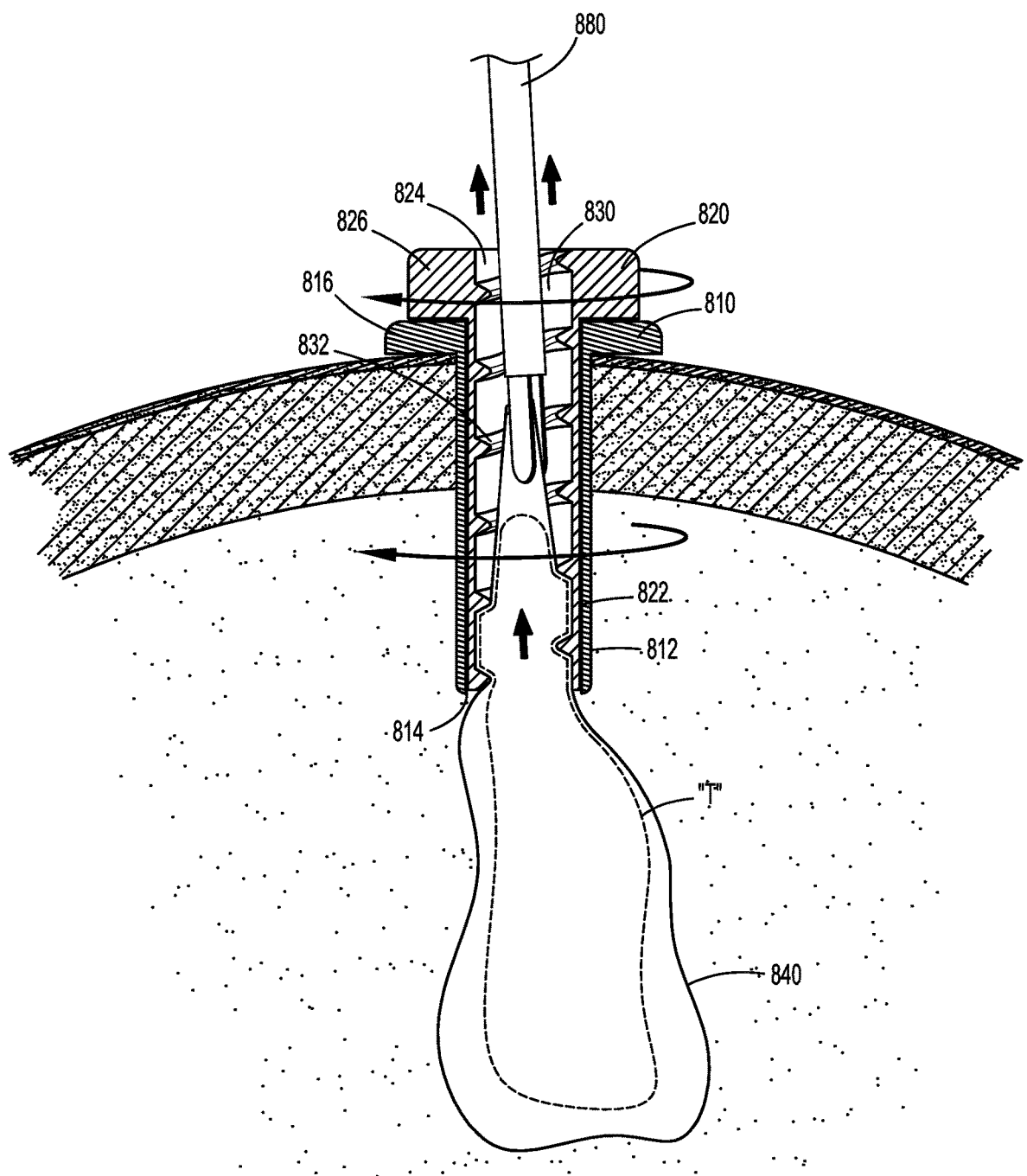

Referring also to FIG. 33, with tissue "T" retained within the closed specimen bag 840 and outer and inner cannulas 810, 820, respectively, in position, specimen bag 840 and the tissue "T" therein can be withdrawn from the internal surgical site. In order to withdraw, specimen bag 840 and the tissue "T" therein, a pull string 870 (FIG. 32) and/or a grasper 880 (FIG. 33) is utilized to pull specimen bag 840 proximally into longitudinal passageway 824 of tubular body 822 of inner cannula 820.

As specimen bag 840 is pulled proximally into longitudinal passageway 824 of tubular body 822 of inner cannula 820, inner cannula 820 is rotated relative to specimen bag 840 and outer cannula 810 in a direction corresponding to the direction of pitch of threading 832. Thus, threading 832 provides torsional urging to feed specimen bag 840 proximally through longitudinal passageway 824 of tubular body 822 of inner cannula 820, thus facilitate withdrawal of specimen bag 840 and the tissue "T" therein from the internal surgical site.

In embodiments, rather than the specimen bag 840 including the tissue "T" therein being fed proximally through longitudinal passageway 824 of tubular body 822 of inner cannula 820, mouth 842 of specimen bag 840 may be exteriorized and outer and inner cannulas 810, 820 may be inserted into specimen bag 840 allowing tissue "T," while isolated from surrounding tissue, to be fed proximally through longitudinal passageway 824 of tubular body 822 of inner cannula 820 and removed from the internal surgical site. Alternatively, specimen bag 840 may be exteriorized through outer cannula 810 with inner cannula 820 inserted into specimen bag 840 allowing tissue "T" to be fed proximally through longitudinal passageway 824 of tubular body 822 of inner cannula 820 and removed from the internal surgical site.

With reference to FIGS. 34-37, still yet another specimen retrieval system 900 is shown. Specimen retrieval system 900 includes a cannula 910, a funnel 920, and a gear system 930 that may be utilized to facilitate removal of a specimen, e.g., tissue "T," enclosed within a specimen bag 940 from an internal surgical site. In embodiments, specimen bag 940 is included as part of specimen retrieval system 900; in other embodiments, specimen bag 940 is separate therefrom enabling use of specimen retrieval system 900 with any other suitable specimen bag or without a specimen bag.

Figure 34:
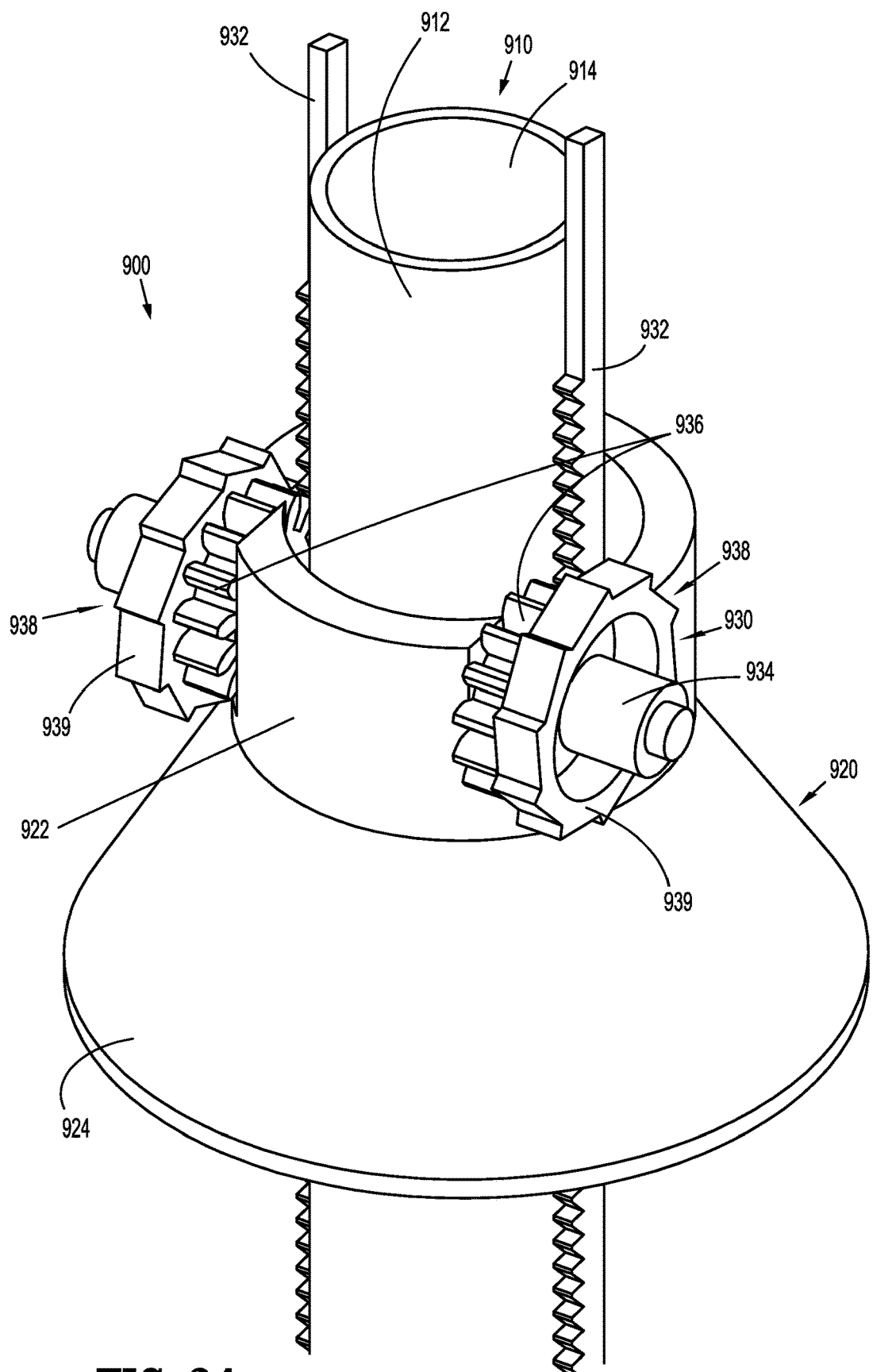
FIG. 34 is a perspective view of a portion of another cannula assembly configured to facilitate withdrawal of a tissue containing specimen bag therethrough.
Figure 35:
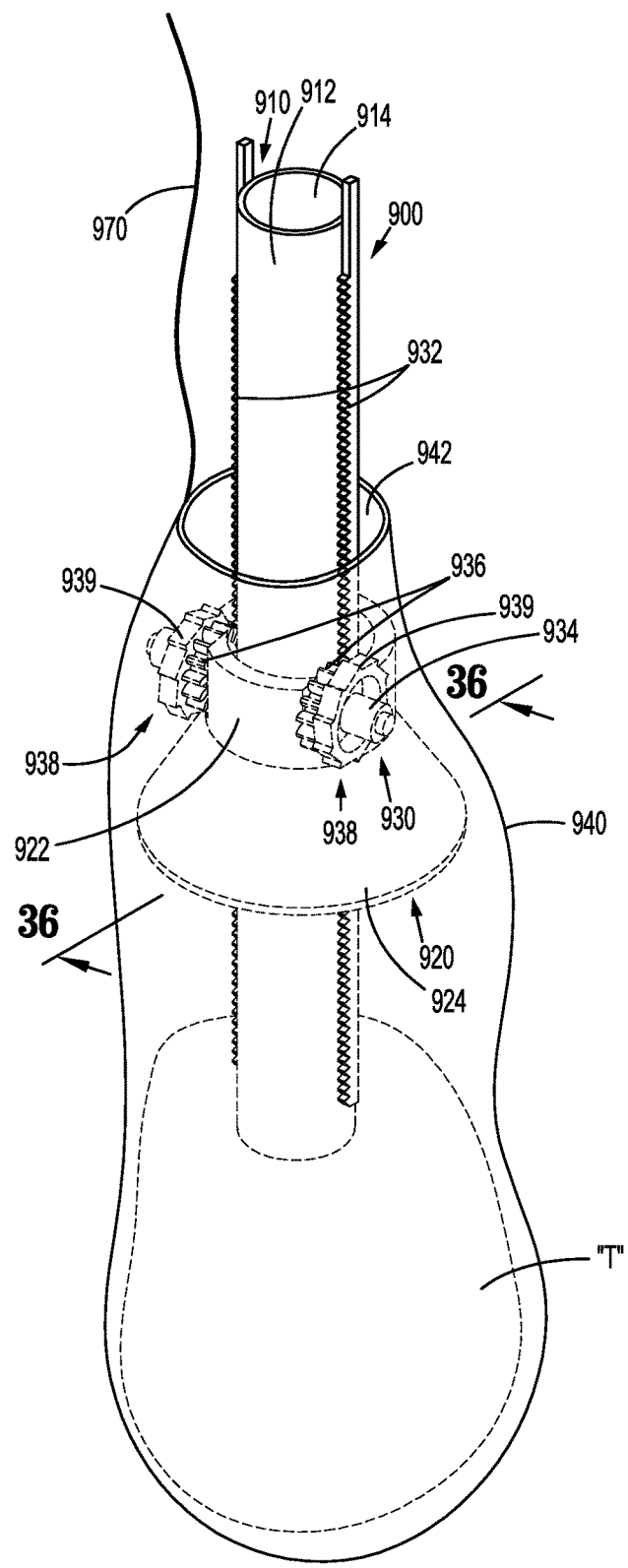
FIG. 35 is a perspective view of the cannula assembly of FIG. 34 disposed within the tissue containing specimen bag.

Referring initially to FIGS. 34 and 35, cannula 910 of specimen retrieval system 900 includes a tubular body 912 defining a longitudinal passageway 914 extending therethrough. Tubular body 912 is configured for insertion through an opening in tissue and into an internal surgical site.

Funnel 920 of specimen retrieval system 900 includes a cylindrical proximal portion 922 and a conical distal portion 924 that extends distally from cylindrical proximal base 922 increasing in diameter in a proximal-to-distal direction. Funnel 920 is slidably disposed about tubular body 912 of cannula 910. Funnel 920 may be formed from a flexible material enabling flexion of funnel 920 to enable insertion through an opening in tissue and into an internal surgical site. Alternatively, funnel 920 may include first and second components, e.g., halves, that are releasably engaged with one another such that the components may be inserted through an opening in tissue and into an internal surgical site separately and then engaged with one another to form funnel 920. As another alternative, funnel 920 may be configured to pivot relative to cannula 910 and/or may include portions configured to pivot and/or slide relative to one another to facilitate insertion through an opening in tissue and into an internal surgical site. Other configurations, including combinations of the above, enabling insertion of funnel 920 through an opening in tissue and into an internal surgical site are also contemplated.

Gear system 930 includes at least one rack 932 disposed on, e.g., formed with, adhered to, mechanically engaged with, etc., and extending longitudinally along an outer surface of tubular body 912 of cannula 910. In embodiments, a pair of spaced-apart and parallel racks 932 extends longitudinally along the outer surface of tubular body 912 of cannula 910. Gear assembly 930 further includes an axle 934 rotatably mounted on and/or within cylindrical proximal base 922 of funnel 920 with at least one end portion of axle 934 extending outwardly from cylindrical proximal base 922 of funnel 920. In embodiments, both end portions of axle 934 extend from funnel 920. At least one gear 936 is mounted on the at least one end portion of axle 934 and disposed in meshed engagement with the at least one rack 932. In embodiments, two racks 932 and gears 936 are provided with each gear 936 disposed in meshed engagement with one of the racks 932. Gear assembly 930 further includes at least one ratchet assembly 938 having a spring-loaded ratchet gear 939 mounted on the at least one end portion of axle 934 and a ratchet pawl (not shown) operably positioned relative to the ratchet gear 939. Gear assembly 930 may additionally include a release (not shown), e.g., a push-button, lever, etc., configured to disengage ratchet gear 939 from the ratchet pawl.

Figure 36:
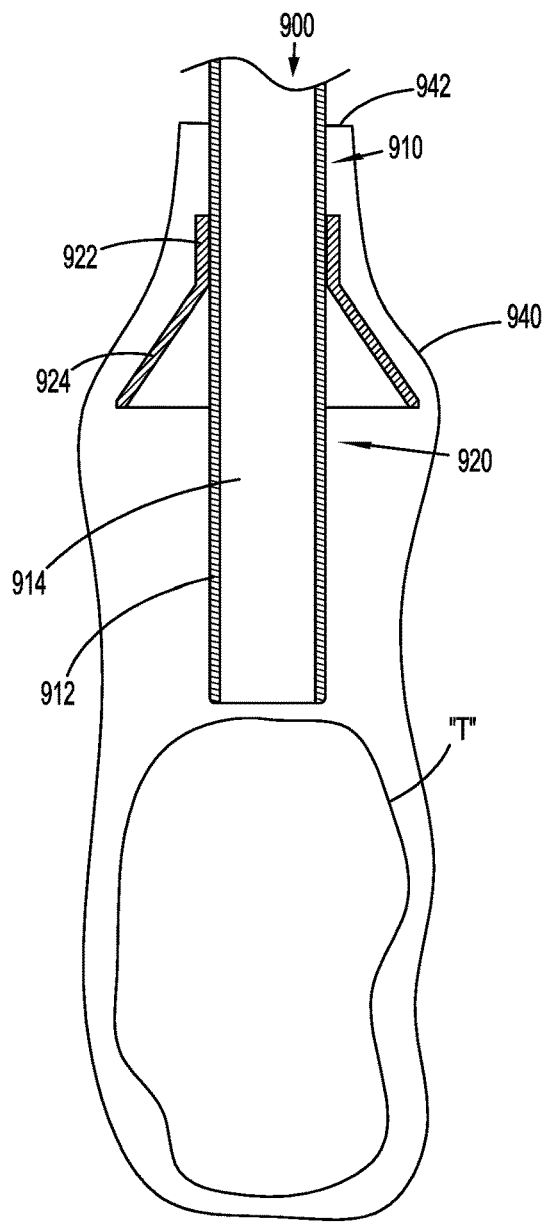
FIGS. 36 and 37 are cross-sectional view progressively illustrating use of the cannula assembly of FIG. 34 for withdrawing the tissue from the specimen bag.
Figure 37:
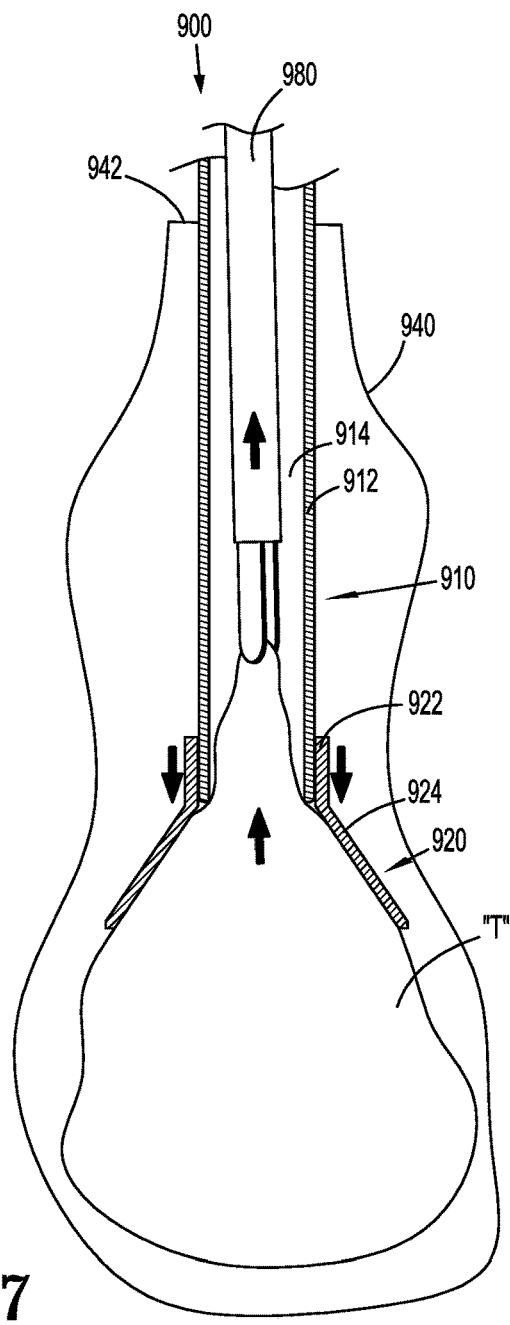

FIGS. 35-37 illustrate use of specimen retrieval system 900. Initially, as shown in FIG. 36, specimen bag 940 is deployed within an internal surgical site and a specimen, e.g., tissue "T," is loaded into specimen bag 940. Next, cannula 910 and funnel 920 are inserted into the internal surgical site (together with one another or separately and then engaged with one another) and through mouth 942 of specimen bag 940 such that at least a portion of cannula 910 and funnel 920 are disposed within the interior of specimen bag 940.

As shown in FIGS. 35 and 37, funnel 920 is then slid distally about cannula 910 towards tissue "T." As funnel 920 is slid distally, the meshed engagement between gears 936 and racks 932 drives rotation of gears 936 and, thus, rotation of axle 934. Rotation of axle 934 rotates ratchet gears 939 relative to the corresponding ratchet pawls (not shown) to incrementally lock funnel 920 in position, inhibiting proximal return of funnel 920. In this manner, funnel 920 may be slid distally about cannula 910 to compress tissue "T" and, when released, locks into position relative to cannula 910. In other embodiments, tissue "T" is not compressed but, rather, funnel 920 is slid distally into position adjacent tissue "T."

Turning to FIG. 37, with funnel 920 locked in position about cannula 910, or while funnel 920 is urged distally incrementally locking in position about cannula 910, a grasper 980 may be utilized to pull tissue "T" proximally through funnel 920 and cannula 910. The cone-shaped configuration of conical distal portion 924 of funnel 920 facilitates withdrawal of tissue "T" by directing tissue "T" radially inwardly in a gradual manner, thus reducing the force required for withdrawal.

As an alternative to inserting cannula 910 and funnel 920 into specimen bag 940, specimen bag 940, along with tissue "T" therein, may together be withdrawn through funnel 920 and cannula 910 in a similar manner as detailed above. In embodiments, pull string 970 (FIG. 35) of specimen bag 940 may be utilized to facilitate withdrawal.

Figure 38:
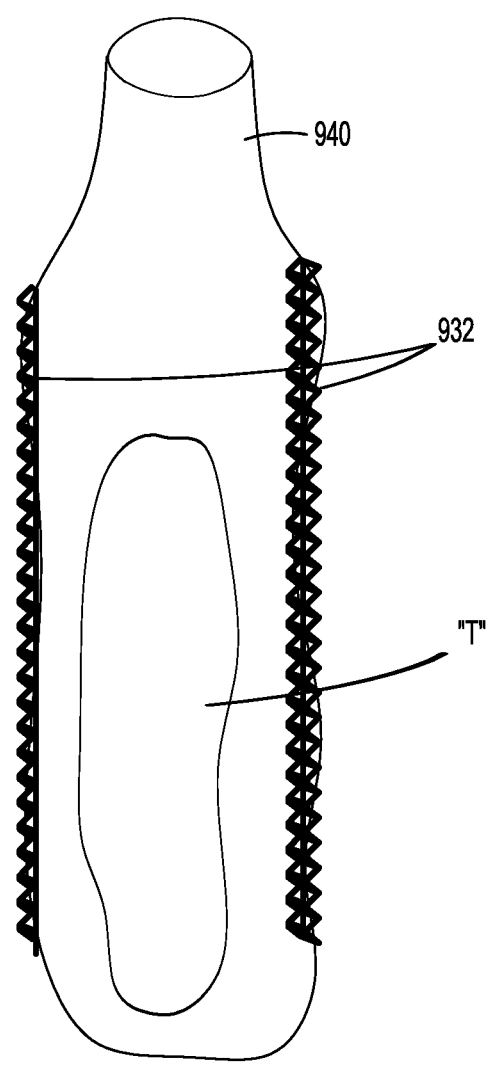
FIG. 38 is a perspective view of another specimen bag configured for use with the funnel of the cannula assembly of FIGS. 34-37.

Referring to FIG. 38, in conjunction with FIGS. 34-37, as an alternative to gear system 930 including a rack 932 disposed on either or both sides of tubular body 912 of cannula 910, racks 932 may be disposed on, e.g., formed with, adhered to, mechanically engaged with, etc., and extend longitudinally along outer surfaces of specimen bag 940 on opposing sides thereof. In such configurations, the ratcheting components associated with funnel 920, e.g., axle 934, gears 936, ratchet assemblies 938, spring-loaded ratchet gears 939, and the ratchet pawls (not shown), may be configured to enable proximal withdrawal of specimen bag 940 (including tissue "T" therein) through funnel 920 while locking to inhibit distal return of specimen bag 940 through funnel 920. In this manner, specimen bag 940 (including tissue "T" therein) may be incrementally (via ratcheting) drawn proximally through funnel 920 (and/or funnel 920 advanced distally over specimen bag 940) to facilitate withdrawal of specimen bag 940 and tissue "T," similarly as detailed above with respect to cannula 910 and funnel 920. In such configurations, conical distal portion 924 of funnel 920 facilitates withdrawal of specimen bag 940 and tissue "T" by urging specimen bag 940 and tissue "T" radially inwardly in a gradual manner as specimen bag 940 is withdrawn through funnel 920, thus reducing the force required for withdrawal. The ratcheting engagement between specimen bag 940 and funnel 920 also facilitates this withdrawal. Cannula 910 may be omitted in such configurations or may be utilized in conjunction with specimen bag 940.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A specimen retrieval system, comprising:
  a specimen bag including a flexible bag body and a biaxial structure, the biaxial structure transitionable between a first condition, wherein the biaxial structure defines a longitudinally compressed and radially expanded configuration, and a second condition, wherein the biaxial structure defines a longitudinally expanded and radially compressed configuration, the biaxial structure biased towards the second condition and configured to transition from the second condition to the first condition in response to a longitudinal pushing force applied to opposing ends of the biaxial structure, wherein the biaxial structure manipulates the flexible bag body such that, in the first condition of the biaxial structure, the specimen bag defines a longitudinally compressed and radially expanded configuration, and such that, in the second condition of the biaxial structure, the specimen bag defines a longitudinally expanded and radially compressed configuration; and
  an insert positionable within the specimen bag and configured, when positioned within the specimen bag, to maintain at least a portion of the biaxial structure in the first condition against the bias of the biaxial structure towards the second condition, thereby maintaining at least a portion of the specimen bag in the longitudinally compressed and radially expanded configuration.

2. The specimen retrieval system according to claim 1, wherein the specimen bag further includes a reinforcement ring surrounding a mouth of the flexible bag body.

3. The specimen retrieval system according to claim 1, wherein the flexible bag body is configured to stretch to accommodate transitioning of the biaxial structure between the first and second conditions.

4. The specimen retrieval system according to claim 1, wherein the insert includes a plurality of fingers extending from a common end portion.

5. The specimen retrieval system according to claim 1, wherein the insert includes a plurality of fingers extending from a base ring.

6. The specimen retrieval system according to claim 1, wherein the insert is compressible from an initial condition to a compressed condition.

7. A specimen retrieval system, comprising:
  a specimen bag including:
    a flexible bag body defining a closed end and an open mouth;
    a reinforcement ring disposed about the open mouth of the flexible bag body and configured to maintain the open mouth of the flexible bag body in an open condition; and
    a biaxial structure biased towards a first condition wherein the biaxial structure defines a longitudinally expanded and radially compressed configuration, the biaxial structure transitionable, in response to a longitudinal pushing force applied to opposing ends of the biaxial structure, from the first condition to a second condition wherein the biaxial structure is longitudinally compressed and radially expanded, wherein the biaxial structure manipulates the flexible bag body such that when the biaxial structure defines the first condition, the specimen bag defines a longitudinally expanded and radially compressed configuration, and such that when the biaxial structure defines the second condition, the specimen bag defines a longitudinally compressed and radially expanded configuration; and an insert positionable within the specimen bag and configured, when positioned within the specimen bag, to maintain at least a portion of the biaxial structure against the bias of the biaxial structure towards the first condition, thereby maintaining at least a portion of the specimen bag in the longitudinally compressed and radially expanded configuration.

8. The specimen retrieval system according to claim 7, wherein the biaxial structure is disposed within the flexible bag body.

9. The specimen retrieval system according to claim 7, wherein the biaxial structure is disposed about the flexible bag body.

10. The specimen retrieval system according to claim 7, wherein the flexible bag body is configured to stretch to accommodate transitioning of the biaxial structure between the first and second conditions.

11. The specimen retrieval system according to claim 7, wherein the insert includes a plurality of fingers extending from a base ring.

12. The specimen retrieval system according to claim 11, wherein each finger of the plurality of fingers defines inwardly-curved free ends.

13. A specimen retrieval system, comprising:
a specimen bag including:
a flexible bag body defining a closed end an open mouth; and
a biaxial structure biased towards a longitudinally expanded and radially compressed configuration, the biaxial structure, in response to a longitudinal pushing force applied to opposing ends of the biaxial structure, configured to longitudinally compress and radially expand against the bias, wherein the biaxial structure manipulates the flexible bag body such that when the biaxial structure is longitudinally expanded and radially compressed, the specimen bag defines a longitudinally expanded and radially compressed configuration, and such that when the biaxial structure is longitudinally compressed and radially expanded, the specimen bag defines a longitudinally compressed and radially expanded configuration; and an insert positionable within the specimen bag and configured, when positioned within the specimen bag, to inhibit at least a portion of the biaxial structure from longitudinally expanding and radially compressing under the bias, thereby maintaining at least a portion of the specimen bag in the longitudinally compressed and radially expanded configuration.

14. The specimen retrieval system according to claim 13, wherein the biaxial structure is disposed within the flexible bag body.

15. The specimen retrieval system according to claim 13, wherein the biaxial structure is disposed about the flexible bag body.

16. The specimen retrieval system according to claim 13, wherein the flexible bag body is configured to stretch to accommodate transitioning of the biaxial structure between the first and second conditions.

17. The specimen retrieval system according to claim 13, wherein the insert includes a plurality of fingers extending from a common end portion.

18. The specimen retrieval system according to claim 17, wherein the plurality of fingers defines a semi-spherical configuration.

* * * * *